(12) United States Patent
Wexler et al.

(10) Patent No.: US 9,213,911 B2
(45) Date of Patent: Dec. 15, 2015

(54) APPARATUS, METHOD, AND COMPUTER READABLE MEDIUM FOR RECOGNIZING TEXT ON A CURVED SURFACE

(71) Applicants: Yonatan Wexler, Jerusalem (IL); Amnon Shashua, Mevasseret Zion (IL)

(72) Inventors: Yonatan Wexler, Jerusalem (IL); Amnon Shashua, Mevasseret Zion (IL)

(73) Assignee: OrCam Technologies Ltd., Jerusalem (IL)

(*) Notice: Subject to any disclaimer, the term of this patent is extended or adjusted under 35 U.S.C. 154(b) by 0 days.

(21) Appl. No.: 14/136,545

(22) Filed: Dec. 20, 2013

(65) Prior Publication Data

US 2014/0267647 A1    Sep. 18, 2014

Related U.S. Application Data

(60) Provisional application No. 61/799,649, filed on Mar. 15, 2013, provisional application No. 61/830,122, filed on Jun. 2, 2013.

(51) Int. Cl.
*G06K 9/32* (2006.01)
*G06K 9/22* (2006.01)
(Continued)

(52) U.S. Cl.
CPC .............. *G06K 9/3275* (2013.01); *A61F 9/08* (2013.01); *G06F 3/011* (2013.01); *G06F 3/16* (2013.01); *G06F 17/2765* (2013.01);
(Continued)

(58) Field of Classification Search
CPC .......... G06K 9/222; G06K 9/224; A61F 9/08; G09B 21/006
USPC .............................. 348/62; 382/114, 181–231
See application file for complete search history.

(56) References Cited

U.S. PATENT DOCUMENTS 4,272,756 A    6/1981   Kakumoto et al.
5,359,675 A *  10/1994  Siwoff ..................... 382/114
(Continued)

FOREIGN PATENT DOCUMENTS

EP   1411460 A2   4/2004
EP   2065871      6/2009
(Continued)

OTHER PUBLICATIONS

J. Liang, D. DeMenthon, & D. Doermann, "Flattening Curved Documents in Images", Feb. 2005 IEEE Comp. Soc. Conf. on Comp. Vision & Pattern Recognition (CVPR 2005) 338-345 (Jun. 2005).*

(Continued)

*Primary Examiner* — Dave Czekaj
*Assistant Examiner* — David N Werner
(74) *Attorney, Agent, or Firm* — Finnegan, Henderson, Farabow, Garrett & Dunner LLP

(57) ABSTRACT

A device and method are provided for recognizing text on a curved surface. In one implementation, the device comprises an image sensor configured to capture from an environment of a user multiple images of text on a curved surface. The device also comprises at least one processor device. The at least one processor device is configured to receive a first image of a first perspective of text on the curved surface, receive a second image of a second perspective of the text on the curved surface, perform optical character recognition on at least parts of each of the first image and the second image, combine results of the optical character recognition on the first image and on the second image, and provide the user with a recognized representation of the text, including a recognized representation of the first portion of text.

24 Claims, 27 Drawing Sheets

(51) Int. Cl.

| | | |
|---|---|---|
| *G06K 9/00* | (2006.01) | |
| *H04N 5/225* | (2006.01) | |
| *G06F 3/16* | (2006.01) | |
| *G06F 3/01* | (2006.01) | |
| *G10L 13/04* | (2013.01) | |
| *G08B 6/00* | (2006.01) | |
| *A61F 9/08* | (2006.01) | |
| *G06F 17/27* | (2006.01) | |
| *G09B 21/00* | (2006.01) | |
| *G08B 3/10* | (2006.01) | |
| *G06K 9/74* | (2006.01) | |
| *G06K 9/20* | (2006.01) | |
| *H04N 5/232* | (2006.01) | |
| *G06T 7/00* | (2006.01) | |
| *G06K 9/30* | (2006.01) | |
| *G01B 11/24* | (2006.01) | |
| *G02C 11/00* | (2006.01) | |

(52) U.S. Cl.
CPC ....... *G06K 9/00221* (2013.01); *G06K 9/00288* (2013.01); *G06K 9/00442* (2013.01); *G06K 9/00463* (2013.01); *G06K 9/00469* (2013.01); *G06K 9/00483* (2013.01); *G06K 9/00671* (2013.01); *G06K 9/2081* (2013.01); *G06K 9/22* (2013.01); *G06K 9/325* (2013.01); *G06K 9/3233* (2013.01); *G06K 9/3241* (2013.01); *G06K 9/3283* (2013.01); *G06K 9/74* (2013.01); *G08B 3/10* (2013.01); *G08B 6/00* (2013.01); *G09B 21/00* (2013.01); *G09B 21/001* (2013.01); *G09B 21/003* (2013.01); *G09B 21/006* (2013.01); *G10L 13/043* (2013.01); *H04N 5/2251* (2013.01); *H04N 5/2252* (2013.01); *H04N 5/23229* (2013.01); *H04N 5/23232* (2013.01); *G01B 11/24* (2013.01); *G02C 11/10* (2013.01); *G06K 9/00852* (2013.01); *G06K 9/30* (2013.01); *G06K 2009/00489* (2013.01); *G06K 2009/2045* (2013.01); *G06T 7/0051* (2013.01)

(56) References Cited

U.S. PATENT DOCUMENTS

| | | | | |
|---|---|---|---|---|
| 5,362,958 | A * | 11/1994 | Ando | 250/208.1 |
| 5,886,342 | A * | 3/1999 | Matsui | 250/208.1 |
| 5,969,829 | A * | 10/1999 | Matsuda et al. | 358/475 |
| 5,995,245 | A * | 11/1999 | Moro | 358/424 |
| 6,014,470 | A * | 1/2000 | Matsuda | 382/275 |
| 6,115,482 | A | 9/2000 | Sears et al. | |
| 6,688,523 | B1 * | 2/2004 | Koenck | 235/462.06 |
| 6,873,732 | B2 * | 3/2005 | Dance | 382/199 |
| 6,940,664 | B1 * | 9/2005 | Pilu | 359/806 |
| 6,970,600 | B2 * | 11/2005 | Abe | 382/187 |
| 6,996,290 | B2 * | 2/2006 | Cariffe | 382/275 |
| 7,072,527 | B1 * | 7/2006 | Nako | 382/290 |
| 7,330,604 | B2 * | 2/2008 | Wu et al. | 382/289 |
| 7,471,848 | B2 * | 12/2008 | Fujimoto et al. | 382/275 |
| 7,486,310 | B2 * | 2/2009 | Sakurai et al. | 348/207.99 |
| 7,508,978 | B1 * | 3/2009 | Lefevere et al. | 382/154 |
| 7,697,776 | B2 * | 4/2010 | Wu et al. | 382/254 |
| 8,218,020 | B2 * | 7/2012 | Tenchio et al. | 348/211.3 |
| 8,285,077 | B2 * | 10/2012 | Fero et al. | 382/290 |
| 8,406,476 | B2 * | 3/2013 | Wu et al. | 382/112 |
| 8,594,387 | B2 * | 11/2013 | Kobeli et al. | 382/114 |
| 8,699,789 | B2 * | 4/2014 | Gordo et al. | 382/159 |
| 2002/0044681 | A1 * | 4/2002 | Fujimoto et al. | 382/154 |
| 2002/0084978 | A1 * | 7/2002 | Araki et al. | 345/156 |
| 2003/0026482 | A1 * | 2/2003 | Dance | 382/199 |
| 2003/0169923 | A1 | 9/2003 | Butterworth | |
| 2003/0198386 | A1 * | 10/2003 | Luo | 382/199 |
| 2003/0198398 | A1 * | 10/2003 | Guan et al. | 382/255 |
| 2004/0042678 | A1 * | 3/2004 | Loce et al. | 382/255 |
| 2005/0041865 | A1 * | 2/2005 | Zhen et al. | 382/187 |
| 2005/0208457 | A1 | 9/2005 | Fink et al. | |
| 2005/0225808 | A1 * | 10/2005 | Braudaway et al. | 358/3.26 |
| 2006/0013444 | A1 | 1/2006 | Kurzweil et al. | |
| 2006/0017810 | A1 | 1/2006 | Kurzweil et al. | |
| 2006/0193533 | A1 * | 8/2006 | Araki et al. | 382/275 |
| 2007/0065040 | A1 | 3/2007 | Ming | |
| 2007/0067713 | A1 | 3/2007 | Ming | |
| 2007/0230748 | A1 * | 10/2007 | Foss | 382/114 |
| 2008/0107345 | A1 * | 5/2008 | Melikian | 382/209 |
| 2008/0112619 | A1 * | 5/2008 | Fujimoto et al. | 382/174 |
| 2008/0240553 | A1 * | 10/2008 | Tamai et al. | 382/162 |
| 2008/0260210 | A1 * | 10/2008 | Kobeli et al. | 382/114 |
| 2008/0267502 | A1 * | 10/2008 | Youngers et al. | 382/176 |
| 2008/0273218 | A1 * | 11/2008 | Kitora et al. | 358/1.13 |
| 2010/0014782 | A1 * | 1/2010 | Fero et al. | 382/290 |
| 2010/0073735 | A1 * | 3/2010 | Hunt et al. | 358/462 |
| 2010/0088099 | A1 * | 4/2010 | Kurzweil et al. | 704/260 |
| 2010/0119158 | A1 * | 5/2010 | Dalal et al. | 382/197 |
| 2010/0220176 | A1 * | 9/2010 | Ziemeck et al. | 348/50 |
| 2011/0222772 | A1 * | 9/2011 | Nijemcevic et al. | 382/182 |
| 2012/0134588 | A1 * | 5/2012 | Zhang et al. | 382/176 |
| 2012/0177291 | A1 * | 7/2012 | Gronau et al. | 382/190 |
| 2012/0212593 | A1 | 8/2012 | Na'aman et al. | |
| 2012/0224072 | A1 * | 9/2012 | Koo et al. | 348/208.2 |
| 2012/0320427 | A1 * | 12/2012 | Zheng et al. | 358/3.26 |
| 2013/0169536 | A1 | 7/2013 | Wexler et al. | |
| 2013/0271584 | A1 | 10/2013 | Wexler et al. | |
| 2013/0343609 | A1 * | 12/2013 | Wilson et al. | 382/103 |
| 2014/0198981 | A1 * | 7/2014 | Wilson et al. | 382/162 |
| 2014/0219561 | A1 * | 8/2014 | Nakamura | 382/176 |

FOREIGN PATENT DOCUMENTS

| | | | |
|---|---|---|---|
| WO | WO 2009/115855 A1 | 9/2009 | |
| WO | WO 2009115855 A1 * | 9/2009 | ............ G06K 9/22 |

OTHER PUBLICATIONS

V. Kluzner & A. Tzadok, "Page Curling Correction for Scanned Books Using Local Distortion Information", 2011 Int'l Conf. on Document Analysis & Recognition 890-894 (Sep. 2011).*

C. Doctorow, "How Google's book-scanner cleverly corrects for the curvature of an open book", Boing Boing, May 3, 2009, http://boingboing.net/2009/05/03/how-googles-book-sca.html.*

D. Doermann, J. Liang, & H. Li, "Progress in Camera-Based Document Image Analysis", 1 Proceedings of 7th Int'l Conf. on Document Analysis & Recognition 606-616 (Aug. 2003).*

J. Liang, D. Doermann, & H. Li, "Camera-based analysis of text and documents: a survey", 7 Int'l J. of Document Analysis & Recognition 84-104 (Jun. 2005).*

S. Lu & C.L. Tam, "Camera Text Recognition based on Perspective Invariants", 2 18th Int'l Conf. on Pattern Recognition 1042-1045 (Aug. 2006).*

Y.Y. Chiang & Craig A. Knoblock, "Recognition of Multi-Oriented, Multi-Sized, and Curved Text", 2011 Int'l Conf. on Document Analysis & Recognition 1399-1403 (Sep. 2011).*

N. Gumerov, A. Zandifar, R. Duraiswami, & L.S. Davis, "Structure of Applicable Surfaces from Single Views", 3023 Lecture Notes in Computer Sci. 482-496 (May 2004).*

J. Pilet, V. Lepetit, & P. Fua, "Fast Non-Rigid Surface Detection, Registration and Realistic Augmentation", 76 Int'l J. of Computer Vision 109-122 (Feb. 2008).*

J. Pilet, V. Lepetit, & P. Fua, "Real-time Non-Rigid Surface Detection", Jan. 2005 IEEE Comp. Soc'y Conf. on Computer Vision & Pattern Recognition 822-828 (Jun. 2005).*

F. Brunet, R. Hartley, A. Bartoli, N. Navab, & R. Malgouyres, "Monocular Template-Based Reconstruction of Smooth and Inextensible Surfaces", 6494 Lecture Notes in Computer Sci. 52-66 (2011).*

M. Sun, R. Yang, L. Yun, G. Landon, B. Seales, & M.S. Brown, "Geometric & Photometric Restoration of Distorted Documents", 2 Tenth IEEE Int'l Conf. on Computer Vision 1117-1123 (Oct. 2005).*

(56) References Cited

OTHER PUBLICATIONS

N. Stamatopoulos, B. Gatos, I. Pratikakis, & S.J. Perantonis, "A Two-Step Dewarping of Camera Document Images", 8 IAPR Int'l Workshop on Document Analysis Systems 209-216 (Sep. 2008).*
M.S. Brown, M. Sun, R. Yang, L. Yun, & W. Brent Seales, "Restoring 2D Content from Distorted Documents", 29 IEEE Transactions on Pattern Analysis & Machine Intelligence 1904-1916 (Nov. 2007).*
F. Courteille, A. Crouzil, J.D. Durou, & P. Gurdjos, "Shape from shading for the digitization of curved documents", 18 Machine Vision & Applications 301-316 (Feb. 2007).*
N.A. Gumerov, A. Zandifar, R. Duraiswami, & L.S. Davis, "3D Structure Recovery and Unwarping of Surfaces Applicable to Planes", 66 Int'l J. of Computer Vision 261-281 (2006).*
Varol, A. Shaji, M. Salzmann, & P. Fua, "Monocular 3D Reconstruction of Locally Textured Surfaces", 34 IEEE Transactions on Pattern Analysis & Machine Intelligence 1118-1130 (Jun. 2012).*
U.S. Appl. No. 14/136,438, filed Dec. 20, 2013, entitled "Apparatus, Method, and Computer Readable Medium for Expedited Text Reading Using Staged OCR Technique."
U.S. Appl. No. 14/135,727, filed Dec. 20, 2013, entitled "Systems and Method for Audible Facial Recognition."
U.S. Appl. No. 14/137,033, filed Dec. 20, 2013, entitled "Apparatus and Method for Providing Failed-Attempt Feedback Using a Camera on Glasses."
U.S. Appl. No. 14/137,263, filed Dec. 20, 2013, entitled "Apparatus and Method for Executing System Commands Based on Captured Image Data."
U.S. Appl. No. 14/135,757, filed Dec. 20, 2013, entitled "Systems and Methods for Automatic Control of a Continuous Action."
U.S. Appl. No. 14/137,373, filed Dec. 20, 2013, entitled "Apparatus and Method for Automatic Action Selection Based on Image Context."
U.S. Appl. No. 14/135,762, filed Dec. 20, 2013, entitled "Systems and Methods for Performing a Triggered Action."
U.S. Appl. No. 14/137,328, filed Dec. 20, 2013, entitled "Apparatus and Method for Performing Actions Based on Captured Image Data."
U.S. Appl. No. 14/135,859, filed Dec. 20, 2013, entitled "Apparatus Connectable to Glasses."
U.S. Appl. No. 14/137,446, filed Dec. 20, 2013, entitled "Apparatus and Method for Hierarchical Object Identification Using a Camera on Glasses."
U.S. Appl. No. 14/135,928, filed Dec. 20, 2013, entitled "Systems and Methods for Processing Images."
U.S. Appl. No. 14/135,775, filed Dec. 20, 2013, entitled "Systems and Methods for Providing Feedback Based on the State of an Object."
U.S. Appl. No. 14/137,522, filed Dec. 20, 2013, entitled "Apparatus and Method for Using Background Change to Determine Context."
U.S. Appl. No. 14/137,384, filed Dec. 20, 2013, entitled "Systems and Methods for Audibly Presenting Textual Information Included in Image Data."
U.S. Appl. No. 14/136,876, filed Dec. 20, 2013, entitled "Apparatus and Method for Analyzing Images."
Karacs, Kristof et al., "Bionic Eyeglass: An Audio Guide for Visually Impaired," Biomedical Circuits and Systems Conference, 2006, BIOCAS 2006, IEEE, Piscataway, NJ, Nov. 29, 2006, p. 190-193.
Lai, Chin-Lun et al., "An Integrated Portable Vision Assistant Agency for the Visual Impaired People," 2009 IEEE International Conference on Control and Automation, Christchurch, New Zealand, Dec. 9-11, 2009 (6 pages).
PCT International Search Report and Written Opinion in corresponding International Application No. PCT/IB2014/001156 dated Oct. 13, 2014, 11 pages.
Yamashita et al., Shape Reconstruction and Image Restoration for Non-Flat Surfaces of Documents with a Stereo Vision System, Proceedings of the 17$^{th}$ International Conference on Pattern Recognition, Aug. 2004, 4 pages.
Guilbourd et al., Stereo Camera Based Wearable Reading Device, Proceedings of the 3$^{rd}$ Augmented Human International Conference, Mar. 2012, 6 pages.
Koo et al., Composition of a Dewarped and Enhanced Document Image From Two View Images, IEEE Transactions on Image Processing, vol. 18, No. 7, Jul. 2009, 12 pages.

* cited by examiner

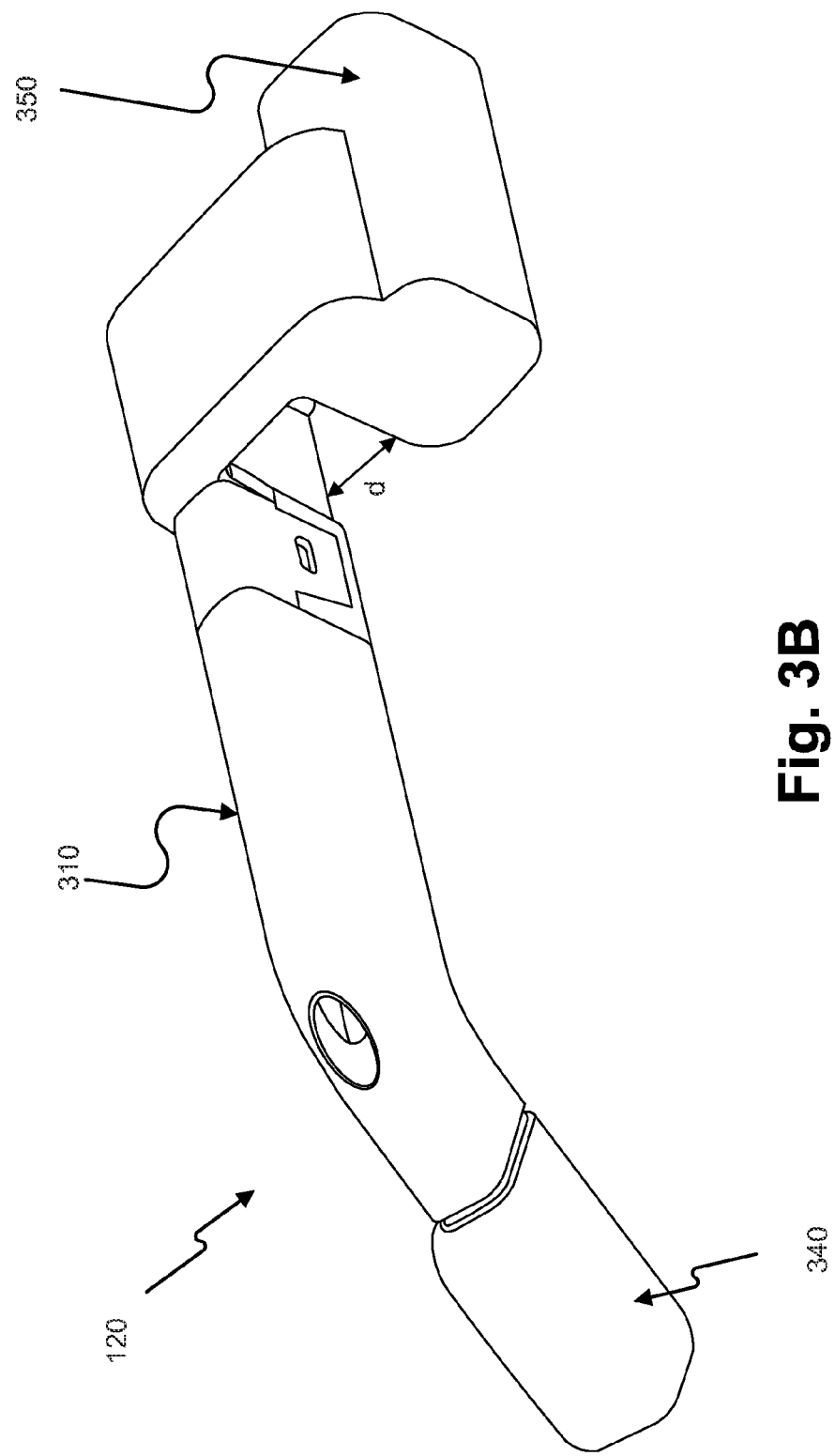

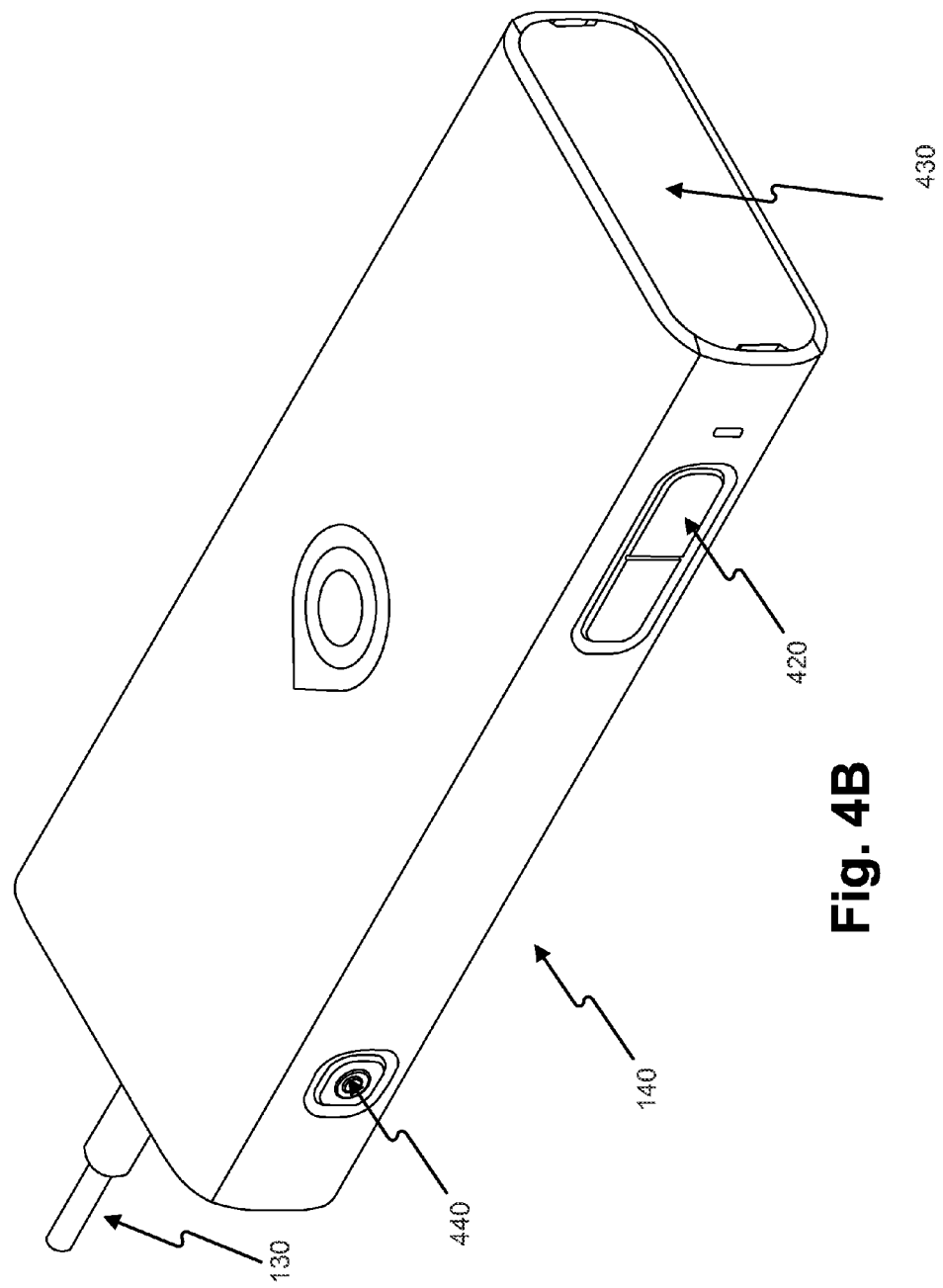

APPARATUS, METHOD, AND COMPUTER READABLE MEDIUM FOR RECOGNIZING TEXT ON A CURVED SURFACE

CROSS REFERENCE TO RELATED APPLICATIONS

This application claims the benefit of priority of U.S. Provisional Patent Application No. 61/799,649, filed on Mar. 15, 2013, and U.S. Provisional Patent Application No. 61/830,122, filed on Jun. 2, 2013, both of which are incorporated herein by reference in their entirety.

BACKGROUND

I. Technical Field

This disclosure generally relates to devices and methods for providing information to a user. More particularly, this disclosure relates to devices and methods for providing information to a user by processing images captured from the environment of the user.

II. Background Information

Visual acuity is an indication of the clarity or clearness of a person's vision that is commonly measured twenty feet from an object. When measuring visual acuity, the ability of a person to identify black symbols on a white background at twenty feet is compared to the ability of a person with normal eyesight. This comparison can be symbolized by a ratio. For example, a ratio of 20/70 vision means a person located at a distance of twenty feet can see what a person with normal vision can see at seventy feet. A person has low vision if he or she has a visual acuity between 20/70 and 20/200 in the better-seeing eye that cannot be corrected or improved with regular eyeglasses. The prevalence of low vision is about one in a hundred for people in their sixties and rapidly increases to one in five for people in their nineties. Low vision may also depend on the environment. For example, some individuals may be able to see only when there is ample light.

A person may have low vision (also known as visual impairment) for several reasons. Other than eye damage and failure of the brain to receive visual cues sent by the eyes, different medical conditions may cause visual impairment. Medical conditions that may cause visual impairment include Age-related Macular Degeneration (AMD), retinitis pigmentosa, cataract, and diabetic retinopathy.

AMD, which usually affects adults, is caused by damage to the retina that diminishes vision in the center of a person's visual field. The lifetime risk for developing AMD is strongly associated with certain genes. For example, the lifetime risk of developing AMD is 50% for people that have a relative with AMD, versus 12% for people that do not have relatives with AMD.

Retinitis pigmentosa is an inherited, degenerative eye disease that causes severe vision impairment and often blindness. The disease process begins with changes in pigment and damage to the small arteries and blood vessels that supply blood to the retina. There is no cure for retinitis pigmentosa and no known treatment can stop the progressive vision loss caused by the disease.

A cataract is a clouding of the lens inside the eye which leads to a decrease in vision. Over time, a yellow-brown pigment is deposited within the lens and obstructs light from passing and being focused onto the retina at the back of the eye. Biological aging is the most common cause of a cataract, but a wide variety of other risk factors (e.g., excessive tanning, diabetes, prolonged steroid use) can cause a cataract.

Diabetic retinopathy is a systemic disease that affects up to 80% of all patients who have had diabetes for ten years or more. Diabetic retinopathy causes microvascular damage to a blood-retinal barrier in the eye and makes the retinal blood vessels more permeable to fluids.

People with low vision experience difficulties due to lack of visual acuity, field-of-view, color perception, and other visual impairments. These difficulties affect many aspects of everyday life. Persons with low vision may use magnifying glasses to compensate for some aspects of low vision. For example, if the smallest letter a person with 20/100 vision can read is five times larger than the smallest letter that a person with 20/20 vision can read, then 5× magnification should make everything that is resolvable to the person with 20/20 vision resolvable to the person with low vision. However, magnifying glasses are expensive and cannot remedy all aspects of low vision. For example, a person with low vision who wears magnifying glasses may still have a difficult time recognizing details from a distance (e.g., people, signboards, traffic lights, etc.). Accordingly, there is a need for other technologies that can assist people who have low vision accomplish everyday activities.

SUMMARY

Embodiments consistent with the present disclosure provide devices and methods for providing information to a user by processing images captured from the environment of the user. The disclosed embodiments may assist persons who have low vision.

In accordance with a disclosed embodiment, an apparatus is provided for recognizing text on a curved surface. The apparatus comprises an image sensor configured to capture from an environment of a user multiple images of text on a curved surface. The apparatus also comprises at least one processor device. The at least one processor device is configured to receive a first image of a first perspective of text on the curved surface. The first image includes a first portion of text unrecognizable in an optical character recognition process. The at least one processor device is further configured to receive a second image of a second perspective of the text on the curved surface. The second image includes the first portion of text in a form capable of recognition in the optical character recognition process. The at least one processor device is further configured to perform optical character recognition on at least parts of each of the first image and the second image, combine results of the optical character recognition on the first image and on the second image, and provide the user with a recognized representation of the text, including a recognized representation of the first portion of text.

In accordance with another disclosed embodiment, an apparatus is provided for recognizing text on a curved surface. The apparatus comprises an image sensor configured to capture from an environment of a user a video stream of text on the curved object. The apparatus also comprises at least one processor device. The at least one processor device is configured to process a first frame of the video stream having a first perspective of text on the curved object. The first frame includes a first portion of text unrecognizable using an optical character recognition process. The at least one processor device is further configured to identify a second frame of the video stream having a second perspective of the text on the curved object. The second frame includes the first portion of text in a form capable of recognition in the optical character recognition process. The at least one processor device is further configured to perform optical character recognition on at least parts of each of the first frame and the second frame, and provide the user with a recognized representation of the text on the curved object, including a recognized representation of the first portion.

In accordance with yet another disclosed embodiment, a method is provided for recognizing text on a curved surface. The method comprises capturing a plurality of images at an initial resolution from an environment of a user, and receiving a first image of a first perspective of text on the curved surface. The first image includes a first portion of text unrecognizable in an optical character recognition process. The method further comprises receiving a second image of a second perspective of the text on the curved surface. The second image includes the first portion of text in a form capable of recognition in an optical character recognition process. The method further comprises performing optical character recognition on at least parts of each of the first image and the second image; combining the results of the optical character recognition on the first image and on the second image and providing the user with a recognized representation of the text, including a recognized representation of the first portion of text.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 3B is a schematic illustration of the sensory unit shown in FIG. 3A from a second viewpoint;

FIG. 4B is a schematic illustration of the processing unit shown in FIG. 4A from a second viewpoint;

DETAILED DESCRIPTION

Figure 1:
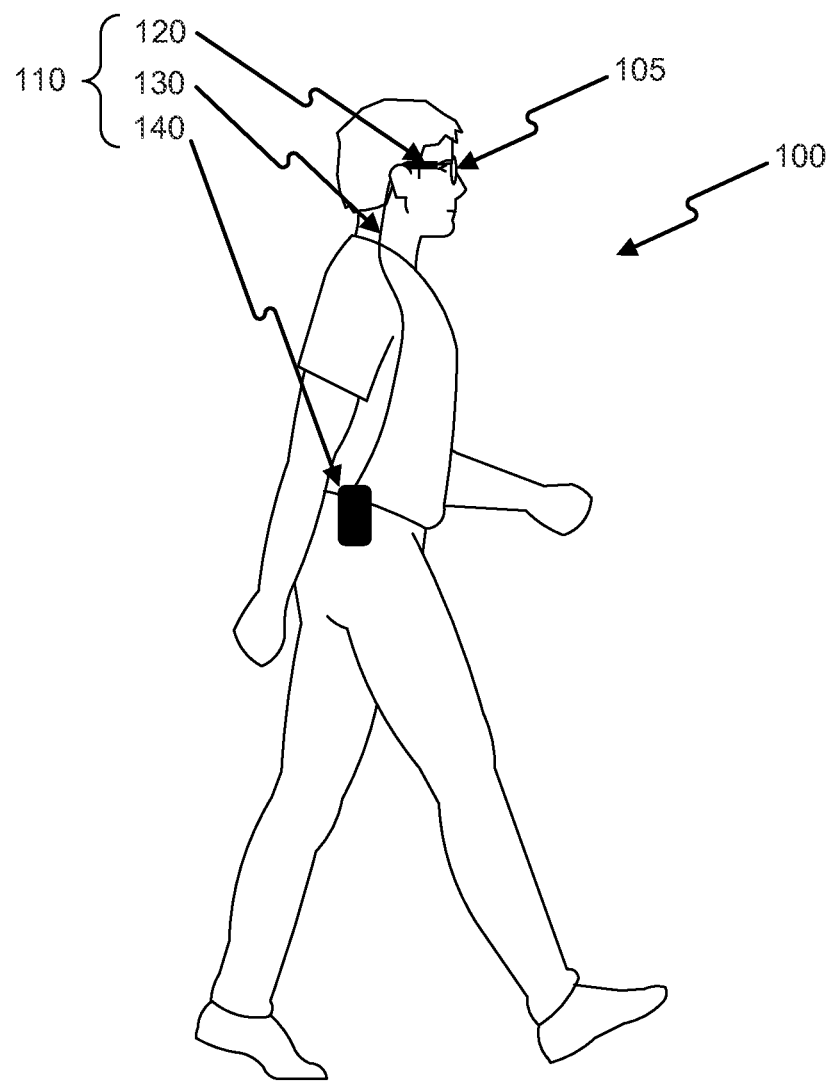
FIG. 1 is a schematic illustration of a user wearing an apparatus for aiding persons who have low vision.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Disclosed embodiments provide devices and methods for assisting people who have low vision. One example of the disclosed embodiments is a device that includes a camera configured to capture real-time image data from the environment of the user. The device also includes a processing unit configured to process the real-time image data and provide real-time feedback to the user. The real-time feedback may include, for example, an output that audibly identifies individuals from a distance, reads signboards, and/or identifies the state of a traffic light.

FIG. 1 illustrates a user 100 wearing an apparatus 110 connected to glasses 105, consistent with a disclosed embodiment. Apparatus 110 may provide functionality for aiding user 100 with various daily activities that are otherwise difficult for user 100 to accomplish due to low vision. Glasses 105 may be prescription glasses, magnifying glasses, non-prescription glasses, safety glasses, sunglasses, etc.

As shown in FIG. 1, apparatus 110 includes a sensory unit 120 and a processing unit 140. Sensory unit 120 may be connected to a support (not shown in FIG. 1) that is mounted on glasses 105. In addition, sensory unit 120 may include an image sensor (not shown in FIG. 1) for capturing real-time image data of the field-of-view of user 100. The term "image data" includes any form of data retrieved from optical signals in the near-infrared, infrared, visible, and ultraviolet spectrums. The image data may be used to form video clips and/or photographs.

Processing unit 140 may communicate wirelessly or via a wire 130 connected to sensory unit 120. In some embodiments, processing unit 140 may produce an output of audible feedback to user 100 (e.g., using a speaker or a bone conduction headphone).

Apparatus 110 is one example of a device capable of implementing the functionality of the disclosed embodiments. Other devices capable of implementing the disclosed embodiments include, for example, a mobile computer with a camera (e.g., a smartphone, a smartwatch, a tablet, etc.) or a clip-on-camera configured to communicate with a processing unit (e.g., a smartphone or a dedicated processing unit, which can be carried in a pocket). A person skilled in the art will appreciate that different types of devices and arrangements of devices may implement the functionality of the disclosed embodiments.

Figure 2A:
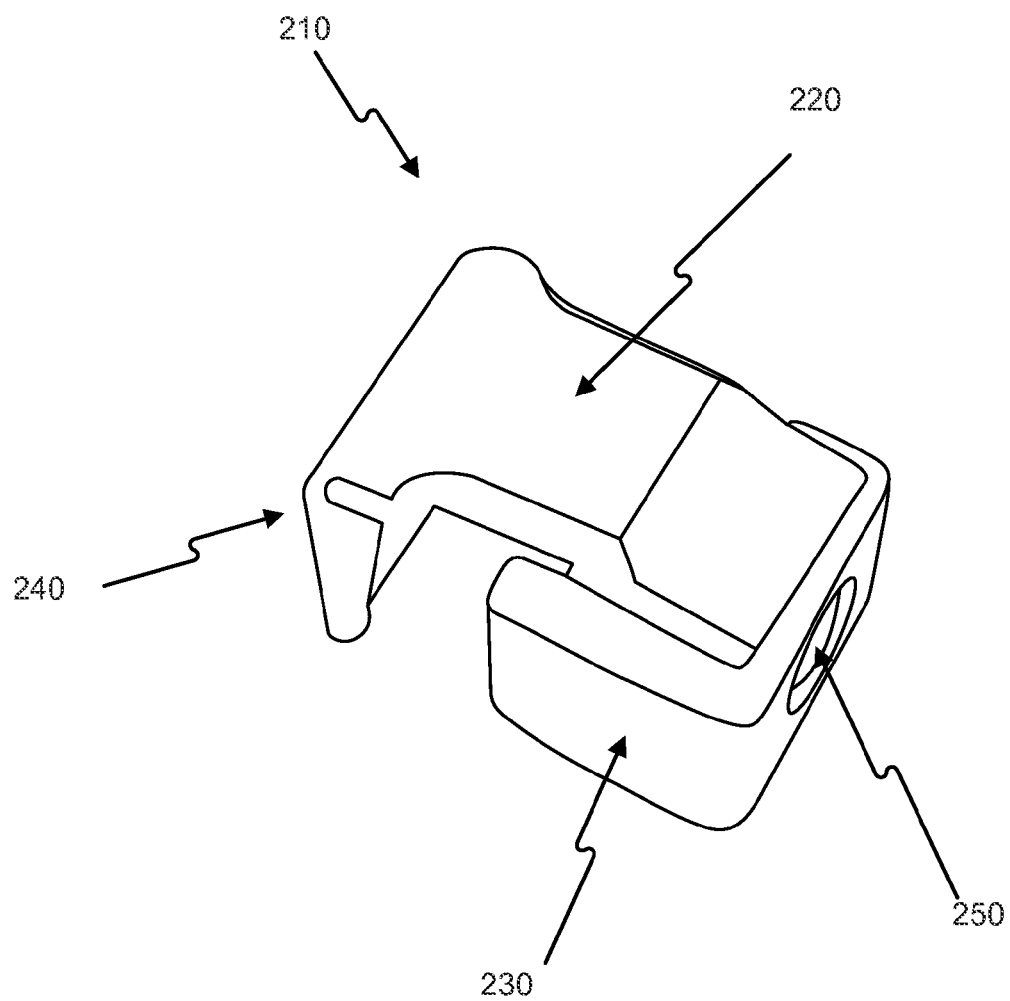
FIG. 2A is a schematic illustration of an example of a support from a first viewpoint.

FIG. 2A is a schematic illustration of an example of a support 210. As discussed in connection with FIG. 1, support 210 may be mounted on glasses 105 and connect to sensory unit 120. The term "support" includes any device or structure that enables detaching and reattaching of a device including a camera to a pair of glasses or to another object (e.g., a helmet). Support 210 may be made from plastic (e.g., polycarbonate), metal (e.g., aluminum), or a combination of plastic and metal (e.g., carbon fiber graphite). Support 210 may be mounted on glasses 105 using screws, bolts, snaps, or any fastening means used in the art.

As shown in FIG. 2A, support 210 includes a base 230 connected to a clamp 240. A bridge 220 connects base 230 with clamp 240. Base 230 and clamp 240 enable sensory unit 120 to easily attach to and detach from support 210. In one embodiment, base 230 may include an internally threaded member 250 for cooperating with a screw (not shown in FIG. 2A) to mount support 210 on glasses 105.

Figure 2B:
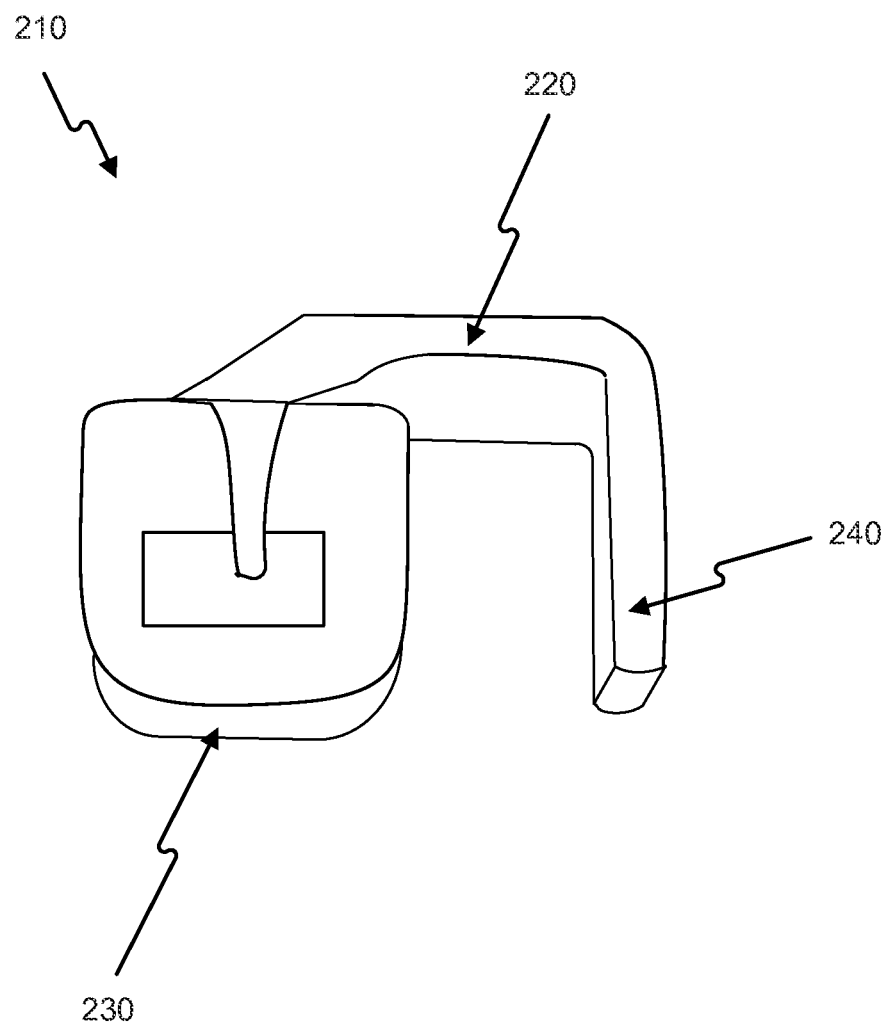
FIG. 2B is a schematic illustration of the support shown in FIG. 2A from a second viewpoint.

FIG. 2B illustrates support 210 from a second viewpoint. The viewpoint shown in FIG. 2B is from a side orientation of support 210.

Figure 2C:
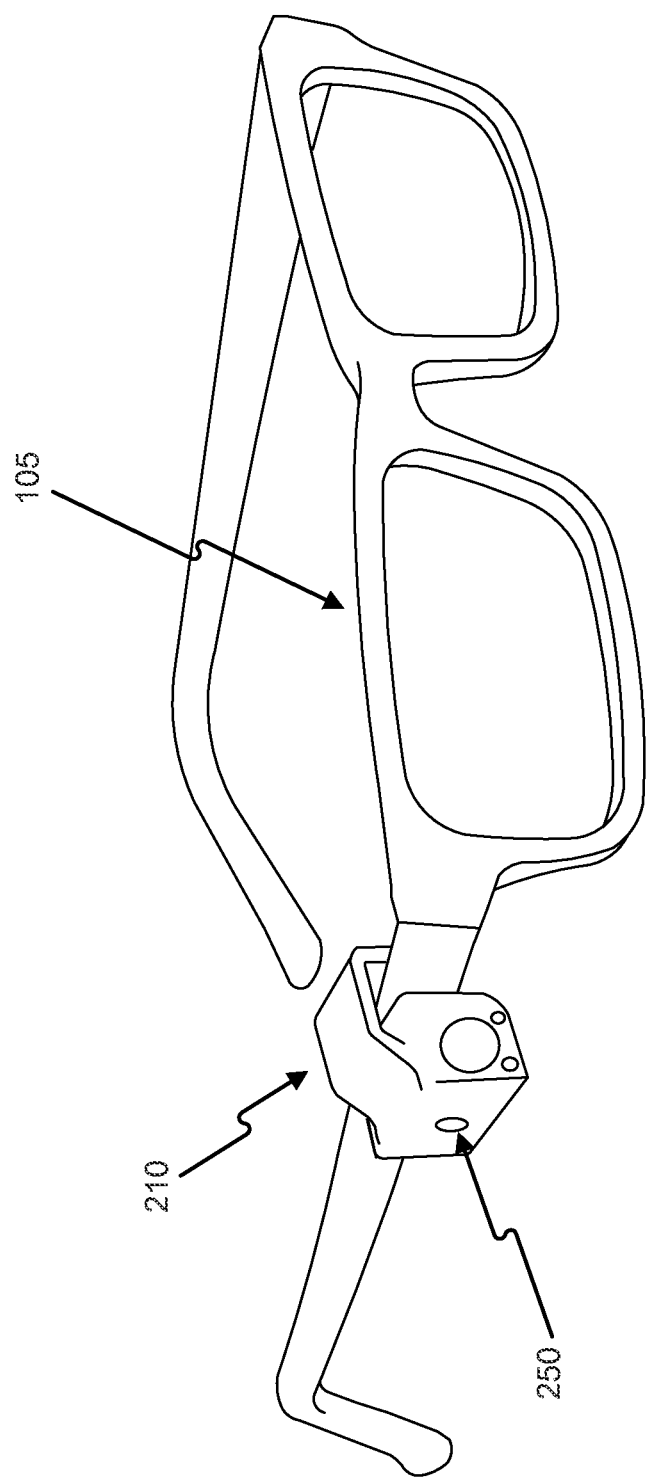
FIG. 2C is a schematic illustration of the support shown in FIG. 2A mounted on a pair of glasses.

FIG. 2C illustrates support 210 mounted on glasses 105. Support 210 may be configured for mounting on any kind of glasses (e.g., eyeglasses, sunglasses, 3D glasses, safety glasses, etc.). As shown in FIG. 2C, sensory unit 120 is not attached to support 210 and, accordingly, support 210 may be sold separately from apparatus 110. This arrangement makes apparatus 110 compatible with a variety of glasses. For example, some users may have several pairs of glasses and may wish to mount a support on each pair of glasses.

In other embodiments, support 210 may be an integral part of a pair of glasses, or sold and installed by an optometrist. For example, support 210 may be configured for mounting on the arms of glasses 105 near the frame front, but before the hinge. Alternatively, support 210 may be configured for mounting on the bridge of glasses 105.

Figure 2D:
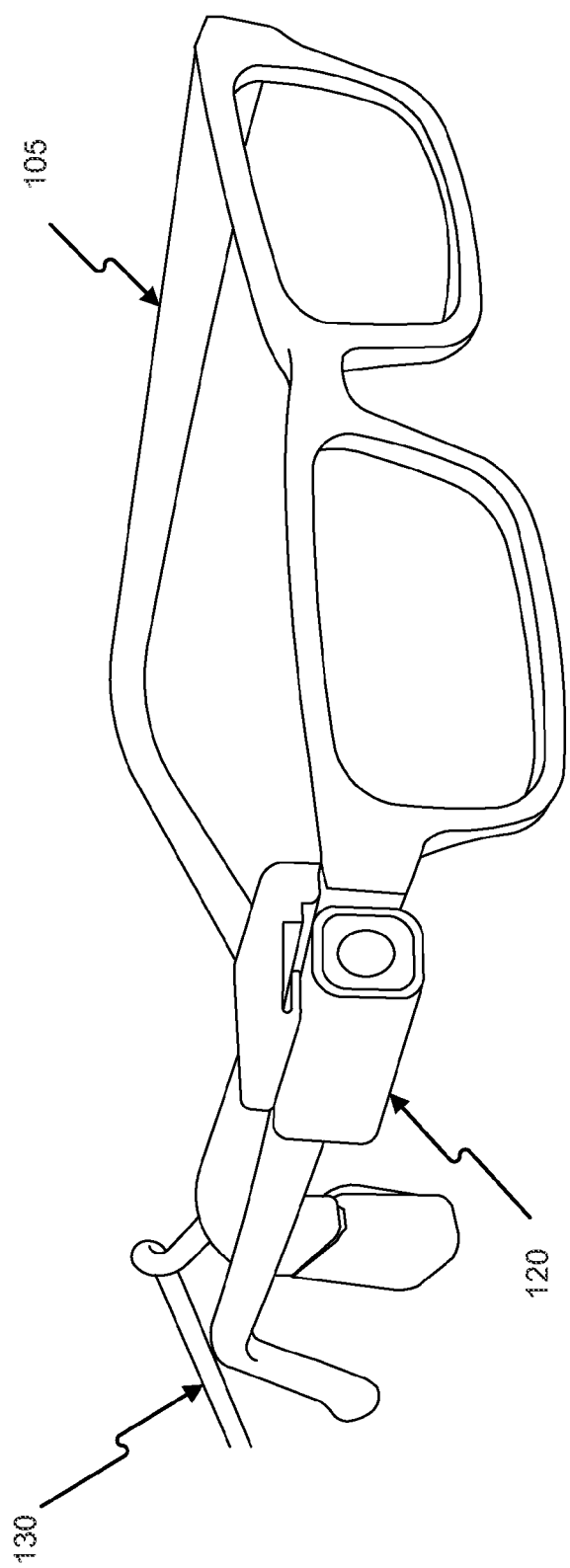
FIG. 2D is a schematic illustration of a sensory unit attached to the support that is mounted on the pair of glasses shown in FIG. 2C.

FIG. 2D illustrates sensory unit 120 attached to support 210 (not visible in FIG. 2D), and support 210 mounted on glasses 105. In some embodiments, support 210 may include a quick release mechanism for disengaging and reengaging sensory unit 120. For example, support 210 and sensory unit 120 may include magnetic elements. As an alternative example, support 210 may include a male latch member and sensory unit 120 may include a female receptacle.

When sensory unit 120 is attached (or reattached) to support 210, the field-of-view of a camera associated with sensory unit 120 may be substantially identical to the field-of-view of user 100. Accordingly, in some embodiments, after support 210 is attached to sensory unit 120, directional calibration of sensory unit 120 may not be required because sensory unit 120 aligns with the field-of-view of user 100.

In other embodiments, support 210 may include an adjustment component (not shown in FIG. 2D) to enable calibration of the aiming direction of sensory unit 120 in a substantially set position that is customized to user 100 wearing glasses 105. For example, the adjustment component may include an adjustable hinge to enable vertical and horizontal alignment of the aiming direction of sensory unit 120. Adjusting the alignment of sensory unit 120 may assist users who have a unique and individual visual impairment. The adjustment may be internal or external to sensory unit 120.

Figure 2E:
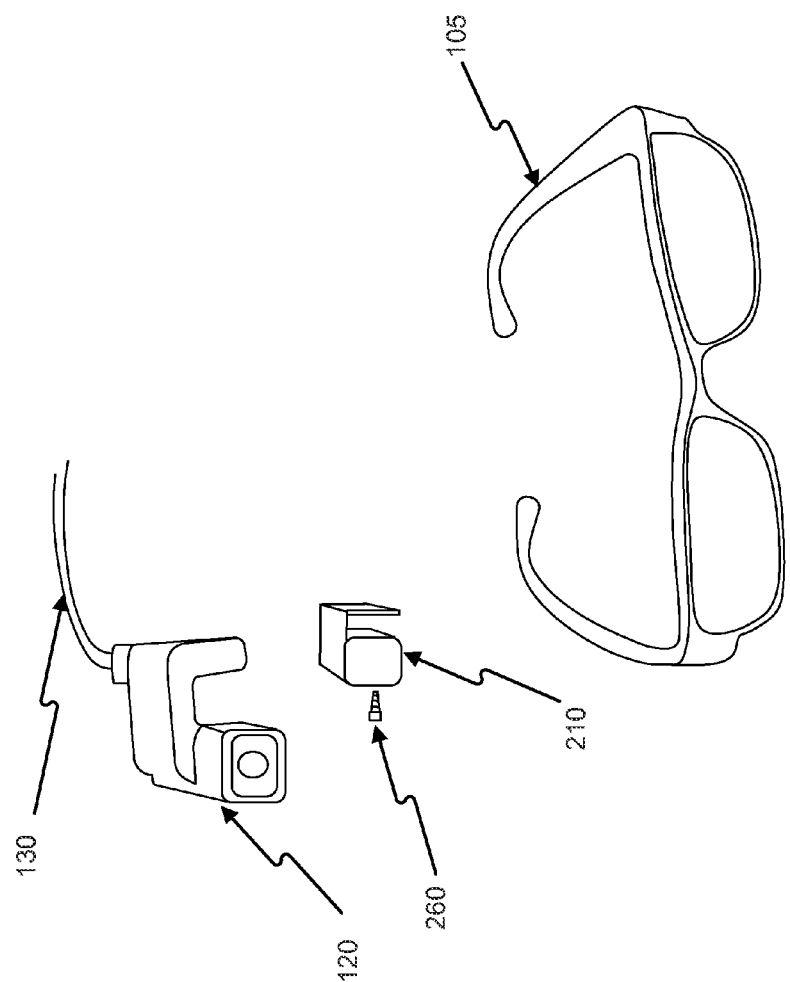
FIG. 2E is an exploded view of FIG. 2D.

FIG. 2E is an exploded view of the components shown in FIG. 2D. Sensory unit 120 may be attached to glasses 105 in the following way. Initially, support 210 may be mounted on glasses 105 using screw 260. Next, screw 260 may be inserted into internally threaded member 250 (not shown in FIG. 2E) in the side of support 210. Sensory unit 120 may then be clipped on support 210 such that it is aligned with the field-of-view of user 100.

Figure 3A:
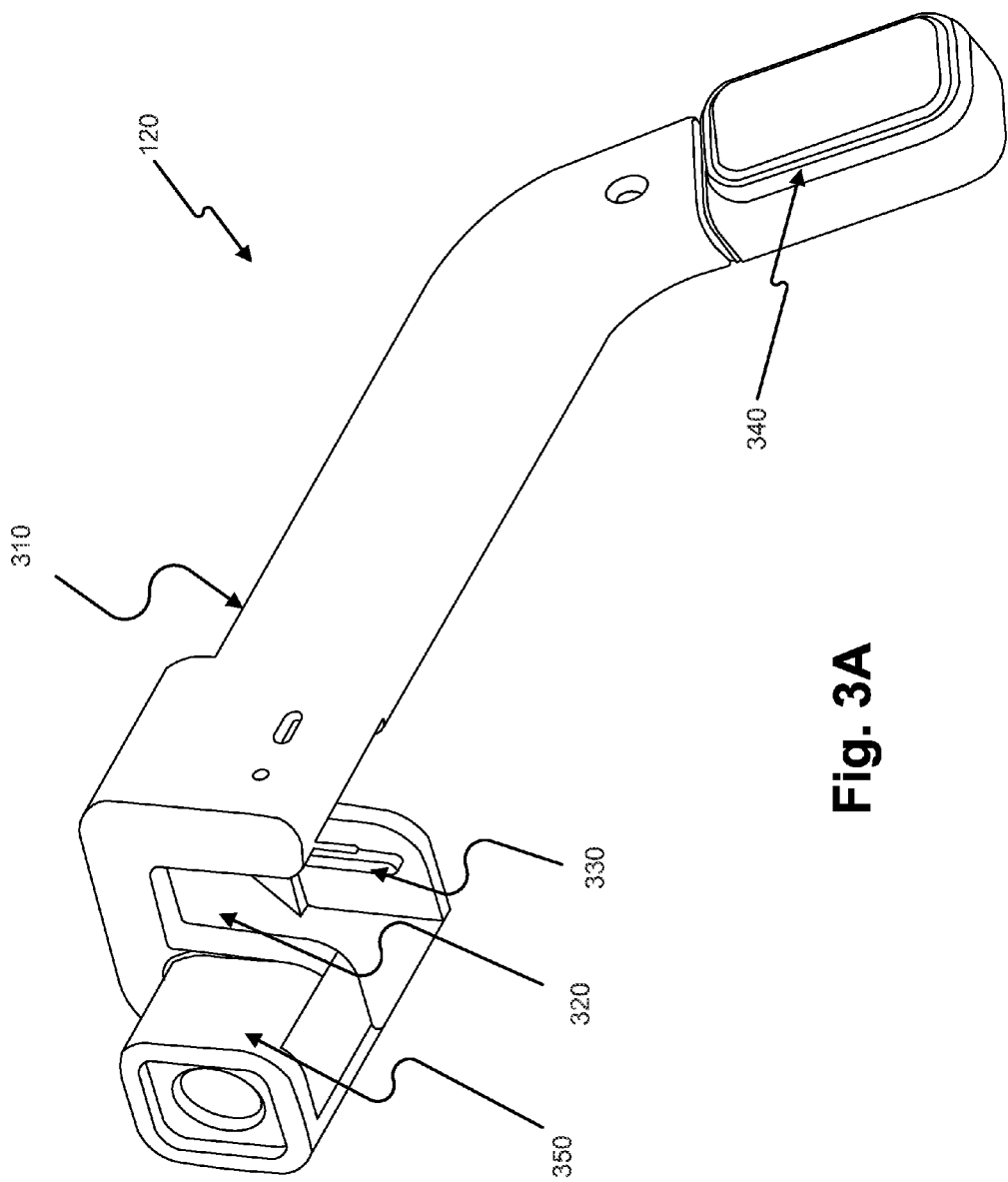
FIG. 3A is a schematic illustration of an example of a sensory unit from a first viewpoint.

FIG. 3A is a schematic illustration of sensory unit 120 from a first viewpoint. As shown in FIG. 3A, sensory unit 120 includes a feedback-outputting unit 340 and an image sensor 350.

Sensory unit 120 is configured to cooperate with support 210 using clip 330 and groove 320, which fits the dimensions of support 210. The term "sensory unit" refers to any electronic device configured to capture real-time images and provide a non-visual output. Furthermore, as discussed above, sensory unit 120 includes feedback-outputting unit 340. The term "feedback-outputting unit" includes any device configured to provide information to a user.

In some embodiments, feedback-outputting unit 340 may be configured to be used by blind persons and persons with low vision. Accordingly, feedback-outputting unit 340 may be configured to output nonvisual feedback. The term "feedback" refers to any output or information provided in response to processing at least one image in an environment. For example, feedback may include a descriptor of a branded product, an audible tone, a tactile response, and/or information previously recorded by user 100. Furthermore, feedback-outputting unit 340 may comprise appropriate components for outputting acoustical and tactile feedback that people with low vision can interpret. For example, feedback-outputting unit 340 may comprise audio headphones, a speaker, a bone conduction headphone, interfaces that provide tactile cues, vibrotactile stimulators, etc.

As discussed above, sensory unit 120 includes image sensor 350. The term "image sensor" refers to a device capable of detecting and converting optical signals in the near-infrared, infrared, visible, and ultraviolet spectrums into electrical signals. The electric signals may be used to form an image based on the detected signal. For example, image sensor 350 may be part of a camera. In some embodiments, when sensory unit 120 is attached to support 210, image sensor 350 may acquire a set aiming direction without the need for directional calibration. The set aiming direction of image sensor 350 may substantially coincide with the field-of-view of user 100 wearing glasses 105. For example, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

As shown in FIG. 3A, feedback-outputting unit 340 and image sensor 350 are included in a housing 310. The term "housing" refers to any structure that at least partially covers, protects, or encloses a sensory unit. The housing may be made from one or more different materials (e.g., plastic or aluminum). In one embodiment, housing 310 may be designed to engage with a specific pair of glasses having a specific support (e.g., support 210). In an alternative embodiment, housing 310 may be designed to engage more than one pair of glasses, each having a support (e.g., support 210) mounted thereon. Housing 310 may include a connector for receiving power from an external mobile-power-source or an internal mobile-power-source, and for providing an electrical connection to image sensor 350.

FIG. 3B is a schematic illustration of sensory unit 120 from a second viewpoint. As shown in FIG. 3B, housing 310 includes a U-shaped element. An inner distance "d" between each side of the U-shaped element is larger than the width of the arm of glasses 105. Additionally, the inner distance "d" between each side of the U-shaped element is substantially equal to a width of support 210. The inner distance "d" between each side of the U-shaped element may allow user 100 to easily attach housing 310 to support 210, which may be mounted on glasses 105. As illustrated in FIG. 3B, image sensor 350 is located on one side of the U-shaped element and feedback-outputting unit 340 is located on another side of the U-shaped element.

Figure 3C:
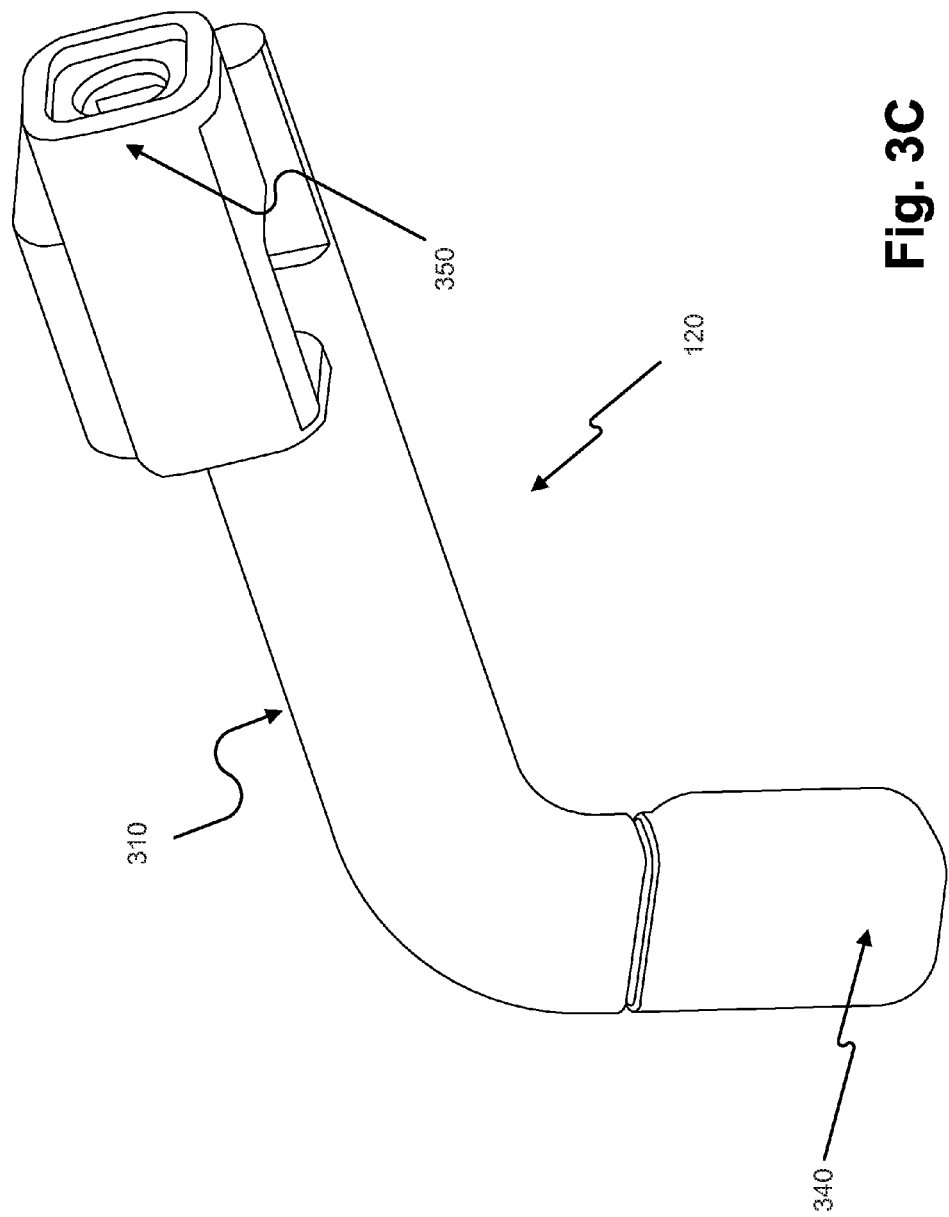
FIG. 3C is a schematic illustration of the sensory unit shown in FIG. 3A from a third viewpoint.

FIG. 3C is a schematic illustration of sensory unit 120 from a third viewpoint. The viewpoint shown in FIG. 3C is from a side orientation of sensory unit 120 and shows the side of the U-shaped element that includes image sensor 350.

Figure 3D:
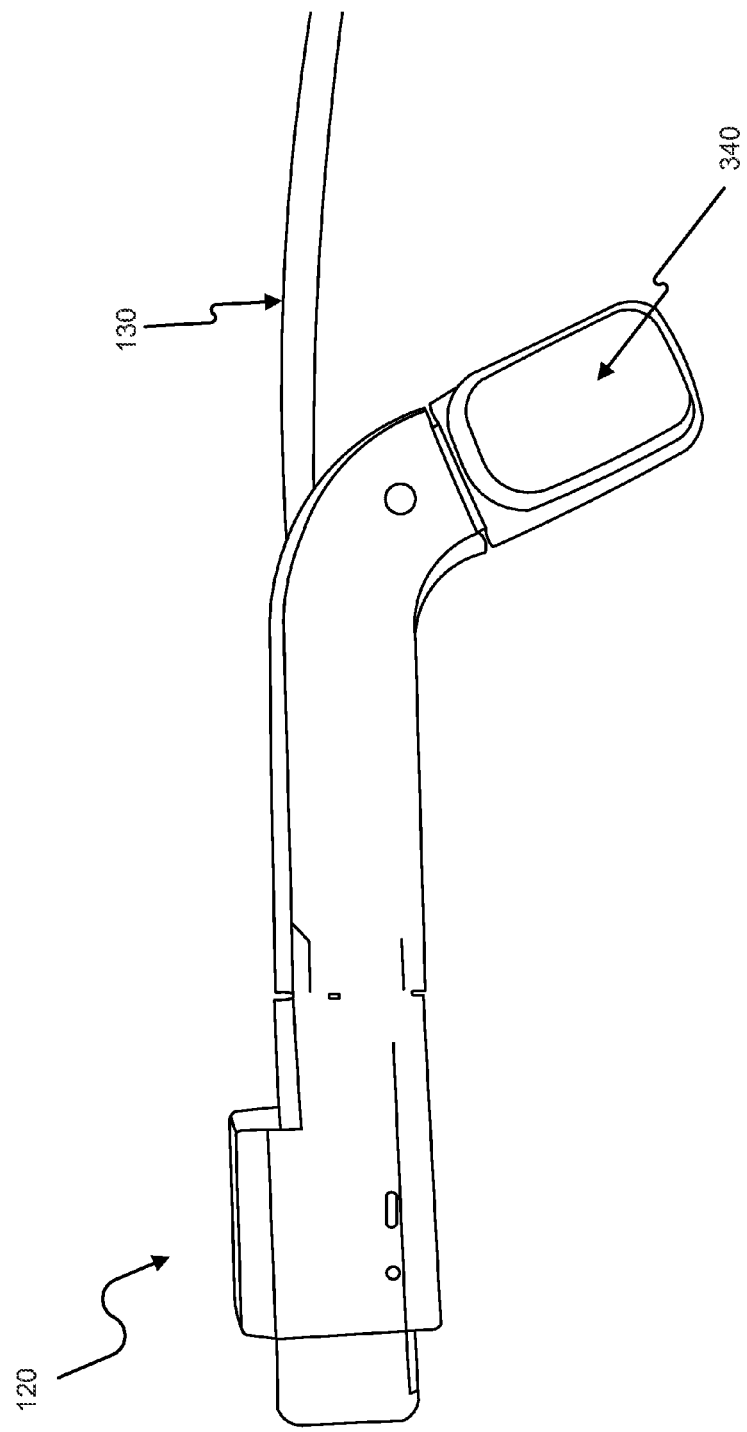
FIG. 3D is a schematic illustration of the sensory unit shown in FIG. 3A from a fourth viewpoint.

FIG. 3D is a schematic illustration of sensory unit 120 from a fourth viewpoint. The viewpoint shown in FIG. 3D is from an opposite side of the orientation shown in FIG. 3C. FIG. 3D shows the side of the U-shaped element that includes feedback-outputting unit 340.

Figure 3E:
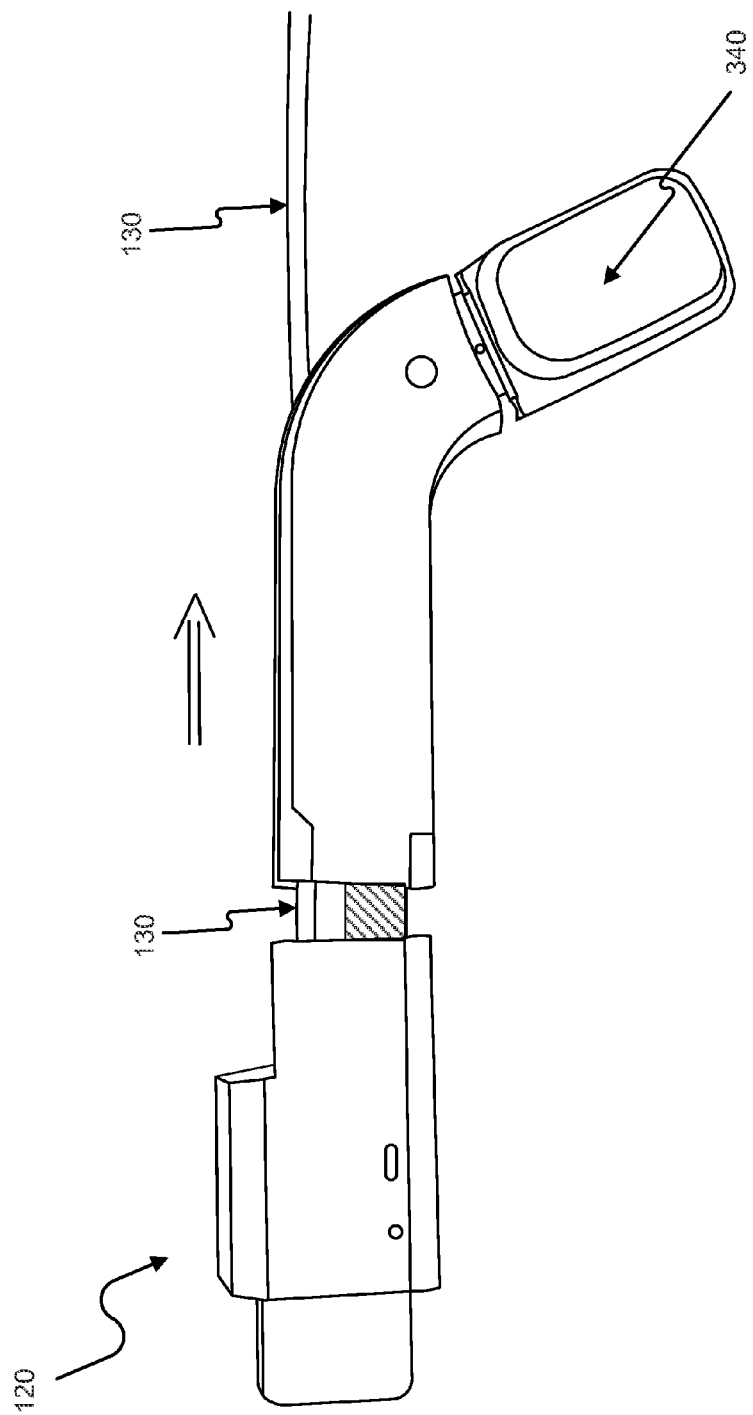
FIG. 3E is a schematic illustration of the sensory unit shown in FIG. 3A in an extended position.

FIG. 3E is a schematic illustration of the sensory unit shown in FIG. 3A in an extended position. As shown in FIG. 3E, a portion of sensory unit 120 is extendable and wire 130 may pass through a channel of sensory unit 120. This arrangement may allow a user to adjust the length and the angle of sensory unit 120 without interfering with the operation of apparatus 110.

User 100 may adjust the U-shaped element of sensory unit 120 so that feedback-outputting unit 340 is positioned adjacent to the user's ear or the user's temple. Accordingly, sensory unit 120 may be adjusted for use with different users who may have different head sizes. Alternatively, a portion of sensory unit 120 may be flexible such that the angle of feedback-outputting unit 340 is relative to the user's ear or the user's temple.

Figure 4A:
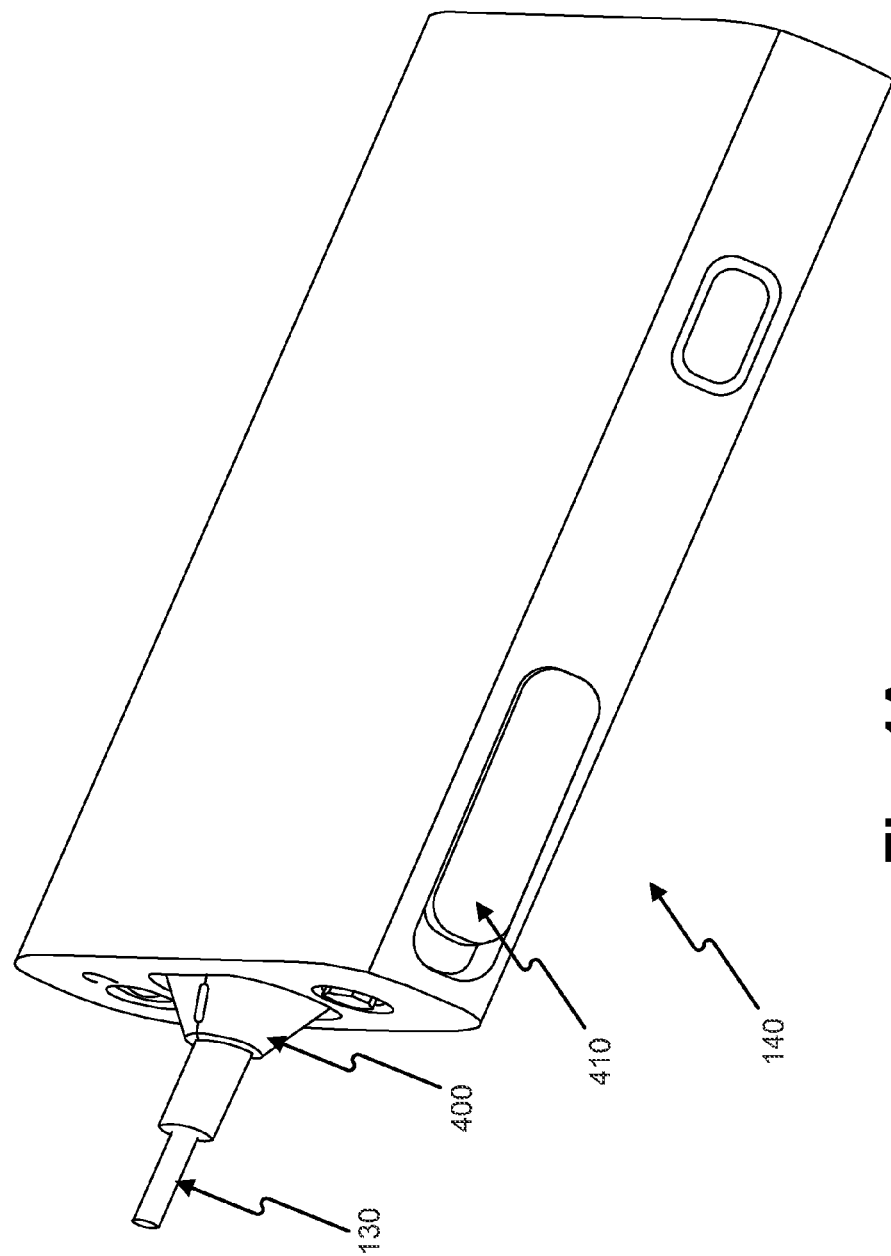
FIG. 4A is a schematic illustration of an example of a processing unit from a first viewpoint.

FIG. 4A is a schematic illustration of processing unit 140. As shown in FIG. 4A, processing unit 140 has a rectangular shape, which easily fits in a pocket of user 100. Processing unit 140 includes a connector 400 for connecting wire 130 to processing unit 140. Wire 130 may be used to transmit power from processing unit 140 to sensory unit 120, and data to and from processing unit 140 to sensory unit 120. Alternatively, wire 130 may comprise multiple wires (e.g., a wire dedicated to power transmission and a wire dedicated to data transmission).

Processing unit 140 includes a function button 410 for enabling user 100 to provide input to apparatus 110. Function button 410 may accept different types of tactile input (e.g., a tap, a click, a double-click, a long press, a right-to-left slide, a left-to-right slide). In some embodiments, each type of input may be associated with a different action. For example, a tap may be associated with the function of confirming an action, while a right-to-left slide may be associated with the function of repeating the last output.

FIG. 4B is a schematic illustration of processing unit 140 from a second viewpoint. As shown in FIG. 4B, processing unit 140 includes a volume switch 420, a battery pack compartment 430, and a power port 440. In one embodiment, user 100 may charge apparatus 110 using a charger connectable to power port 440. Alternatively, user 100 may replace a battery pack (not shown) stored in battery pack compartment 430.

Figure 5A:
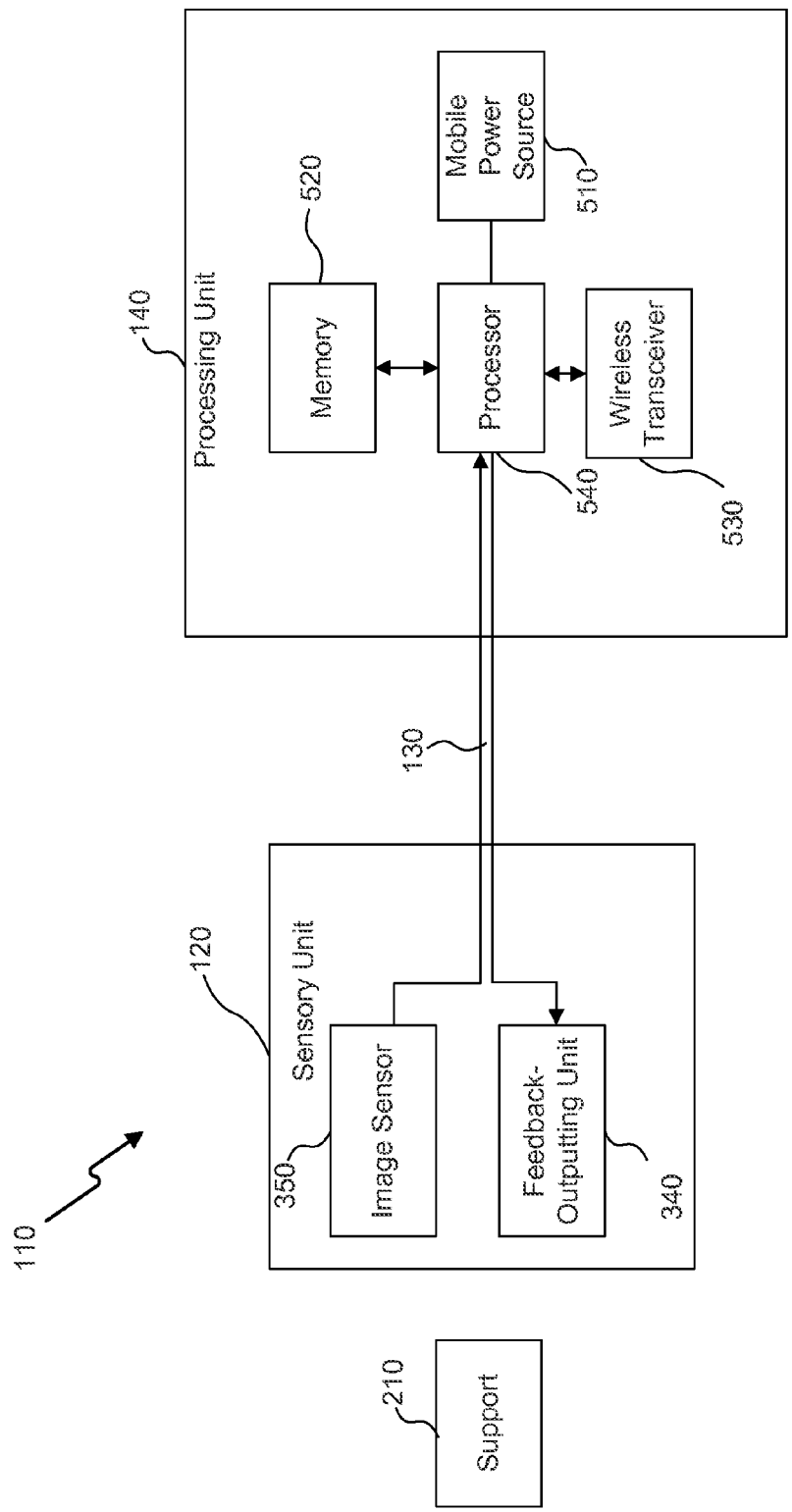
FIG. 5A is a block diagram illustrating an example of the components of an apparatus for aiding persons who have low vision according to a first embodiment.

FIG. 5A is a block diagram illustrating the components of apparatus 110 according to a first embodiment. Specifically, FIG. 5A depicts an embodiment in which apparatus 110 comprises sensory unit 120 and processing unit 140, as discussed in connection with, for example, FIG. 1. Furthermore, sensory unit 120 may be physically coupled to support 210.

As shown in FIG. 5A, sensory unit 120 includes feedback-outputting unit 340 and image sensor 350. Although one image sensor is depicted in FIG. 5A, sensory unit 120 may include a plurality of image sensors (e.g., two image sensors). For example, in an arrangement with more than one image sensor, each of the image sensors may be face a different direction or be associated with a different camera (e.g., a wide angle camera, a narrow angle camera, an IR camera, etc.). In other embodiments (not shown in the figure) sensory unit 120 may also include buttons and other sensors such as a microphone and inertial measurements devices.

As further shown in FIG. 5A, sensory unit 120 is connected to processing unit 140 via wire 130. Processing unit 140 includes a mobile power source 510, a memory 520, a wireless transceiver 530, and a processor 540.

Processor 540 may constitute any physical device having an electric circuit that performs a logic operation on input or inputs. For example, processor 540 may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by processor 540 may, for example, be pre-loaded into a memory integrated with or embedded into processor 540 or may be stored in a separate memory (e.g., memory 520). Memory 520 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although one processor is shown in FIG. 5A, processing unit 140 may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

In some embodiments, processor 540 may change the aiming direction of image sensor 350 using image data provided from image sensor 350. For example, processor 540 may recognize that a user is reading a book and determine that the aiming direction of image sensor 350 is offset from the text. That is, because the words in the beginning of each line of text are not fully in view, processor 540 may determine that image sensor 350 is tilted down and to the right. Responsive thereto, processor 540 may adjust the aiming direction of image sensor 350.

Processor 540 may access memory 520. Memory 520 may be configured to store information specific to user 100. For example, data for image representations of known individuals, favorite products, personal items, etc., may be stored in memory 520. In one embodiment, user 100 may have more than one pair of glasses, with each pair of glasses having support 210 mounted thereon. Accordingly, memory 520 may store information (e.g., personal settings) associated with each pair of glasses. For example, when a user wears his sunglasses may have different preferences than when the user wears reading glasses.

As shown in FIG. 5A, processing unit 140 includes mobile power source 510. Mobile power source 510 may be configured to power processing unit 140 and/or sensory unit 120. The term "mobile power source" includes any device capable of providing electrical power, which can be easily carried by a hand (e.g., the total weight of mobile power source 510 may be less than a pound). Thus, the mobility of the power source enables user 100 to use apparatus 110 in a variety of situations. For example, mobile power source 510 may include one or more batteries (e.g., nickel-cadmium batteries, nickel-metal hydride batteries, and lithium-ion batteries) or any other type of electrical power supply. In some embodiments, mobile power source 510 may be rechargeable and contained within a casing that holds processing unit 140. In other embodiments, mobile power source 510 may include one or more energy harvesting devices for converting ambient energy into electrical energy (e.g., portable solar power units, human vibration units, etc.).

Apparatus 110 may operate in a low-power-consumption mode and in a processing-power-consumption mode. For example, mobile power source 510 can produce five hours of processing-power-consumption mode and fifteen hours of low-power-consumption mode. Accordingly, different power consumption modes may allow mobile power source 510 to produce sufficient power for powering processing unit 140 for various time periods (e.g., more than two hours, more than four hours, more than ten hours, etc.).

Mobile power source 510 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data or audio data) from image sensor 350 to processing unit 140, or wireless transceiver 530 may transmit data from processing unit 140 to feedback-outputting unit 340.

In another embodiment, wireless transceiver 530 may communicate with a different device (e.g., a hearing aid, the user's smartphone, or any wirelessly controlled device) in the environment of user 100. For example, wireless transceiver 530 may communicate with an elevator using a Bluetooth® controller. In such an arrangement, apparatus 110 may recognize that user 100 is approaching an elevator and call the elevator, thereby minimizing wait time. In another example, wireless transceiver 530 may communicate with a smart TV. In such an arrangement, apparatus 110 may recognize that user 100 is watching television and identify specific hand movements as commands for the smart TV (e.g., switching channels). In yet another example, wireless transceiver 530 may communicate with a virtual cane. A virtual cane is any device that uses a laser beam or ultrasound waves to determine the distance from user 100 to an object.

Figure 5B:
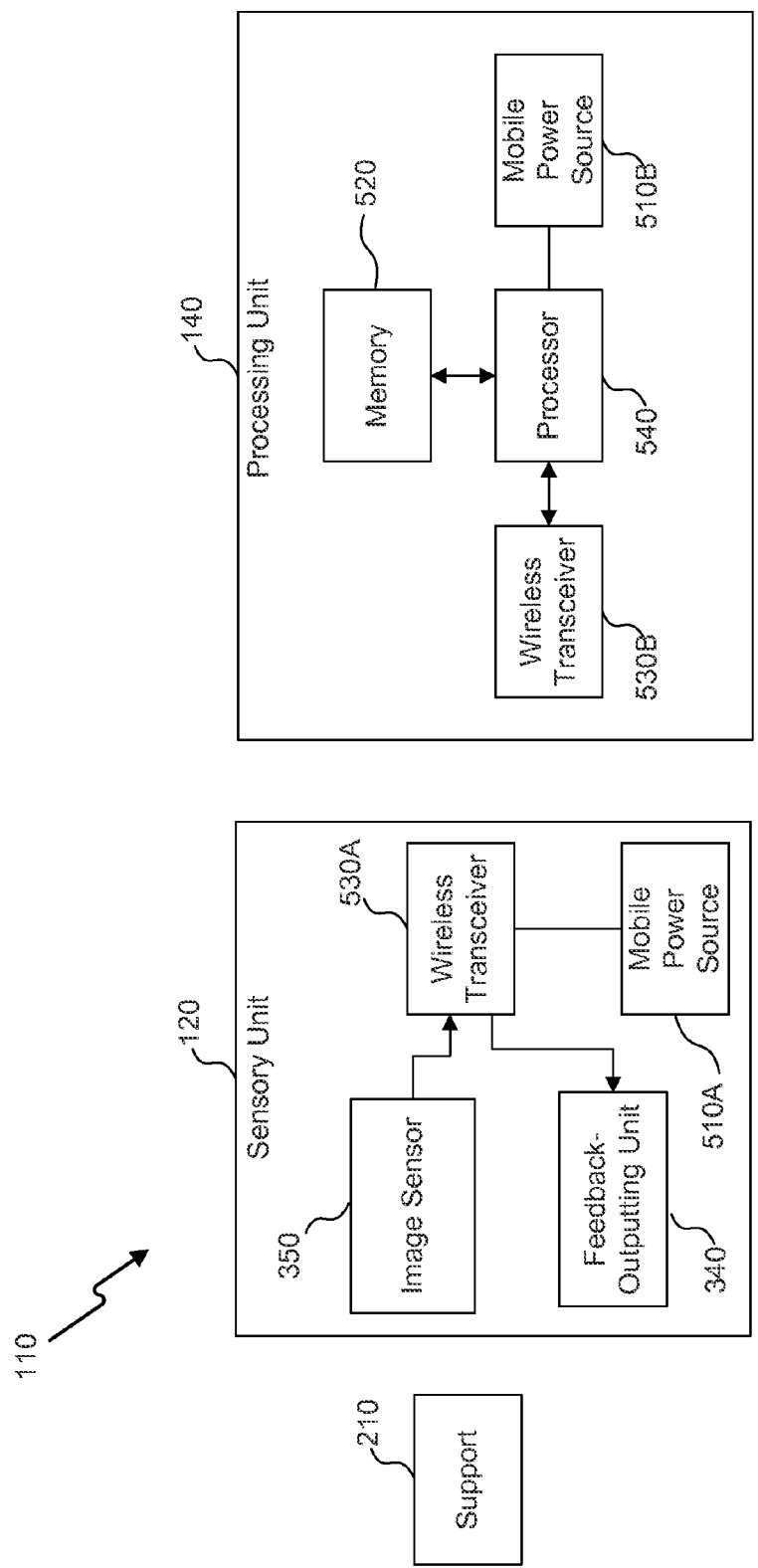
FIG. 5B is a block diagram illustrating an example of the components of an apparatus for aiding persons who have low vision according to a second embodiment.

FIG. 5B is a block diagram illustrating the components of apparatus 110 according to a second embodiment. In FIG. 5B, similar to the arrangement shown in FIG. 5A, support 210 is used to couple sensory unit 120 to a pair of glasses. However, in the embodiment shown in FIG. 5B, sensory unit 120 and processing unit 140 communicate wirelessly. For example, wireless transceiver 530A can transmit image data to processing unit 140 and receive information to be outputted via feedback-outputting unit 340.

In this embodiment, sensory unit 120 includes feedback-outputting unit 340, mobile power source 510A, wireless transceiver 530A, and image sensor 350. Mobile power source 510A is contained within sensory unit 120. As further shown in FIG. 5B, processing unit 140 includes wireless transceiver 530B, processor 540, mobile power source 510B, and memory 520.

Figure 5C:
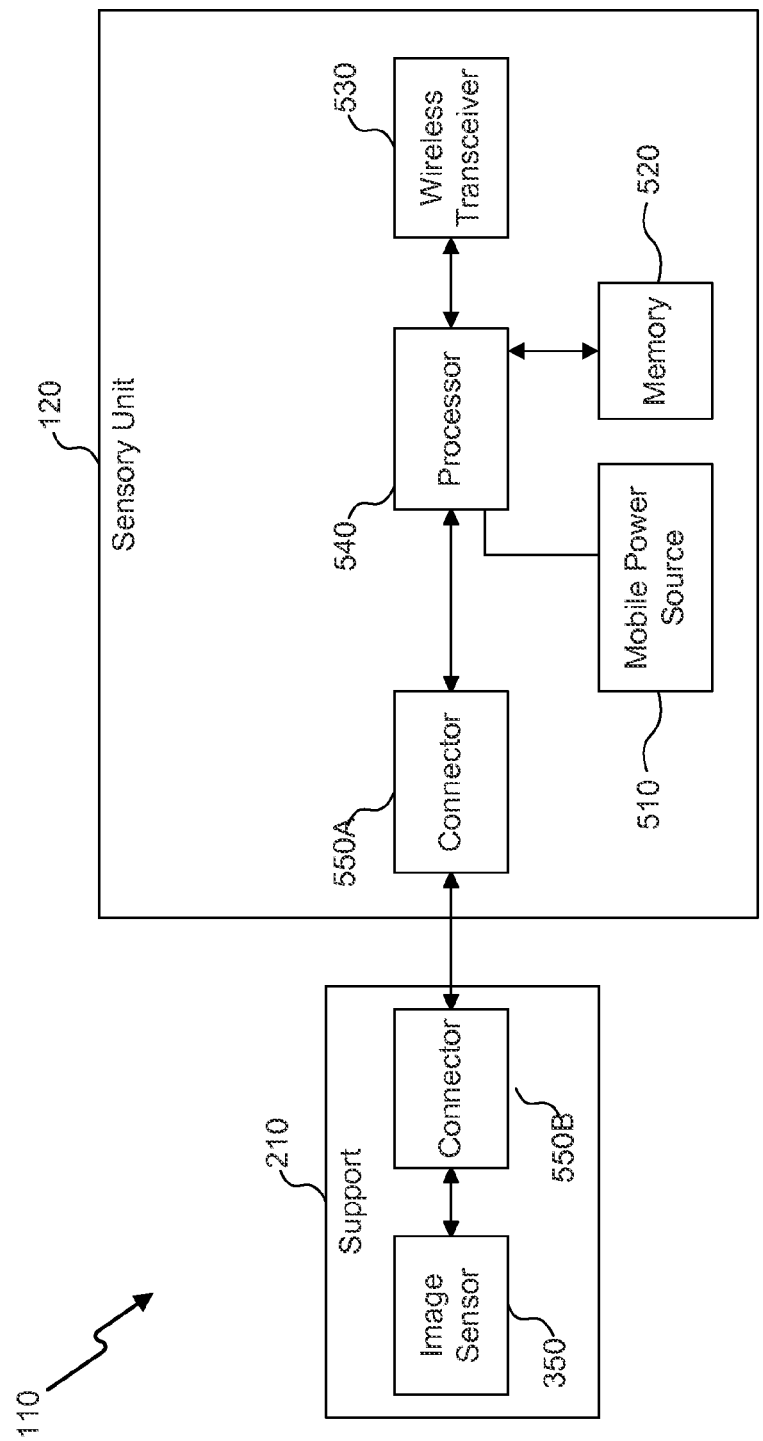
FIG. 5C is a block diagram illustrating an example of the components of an apparatus for aiding persons who have low vision according to a third embodiment.

FIG. 5C is a block diagram illustrating the components of apparatus 110 according to a third embodiment. In particular, FIG. 5C depicts an embodiment in which support 210 includes image sensor 350 and connector 550B. In this embodiment, sensory unit 120 provides functionality for processing data and, therefore, a separate processing unit is not needed in such a configuration.

As shown in FIG. 5C, sensory unit 120 includes processor 540, connector 550A, mobile power source 510, memory 520, and wireless transceiver 530. In this embodiment, apparatus 110 does not include a feedback-outputting unit. Accordingly, wireless transceiver 530 may communicate directly with a hearing aid (e.g., a Bluetooth® hearing aid). In addition, in this embodiment, image sensor 350 is included in support 210. Accordingly, when support 210 is initially mounted on glasses 105, image sensor 350 may acquire a set aiming direction. For example, a camera associated with image sensor 350 may be installed within support 210 in a predetermined angle in a position facing slightly downwards (e.g., 7-12 degrees from the horizon). Furthermore, connector 550A and connector 550B may allow data and power to be transmitted between support 210 and sensory unit 120.

Figure 5D:
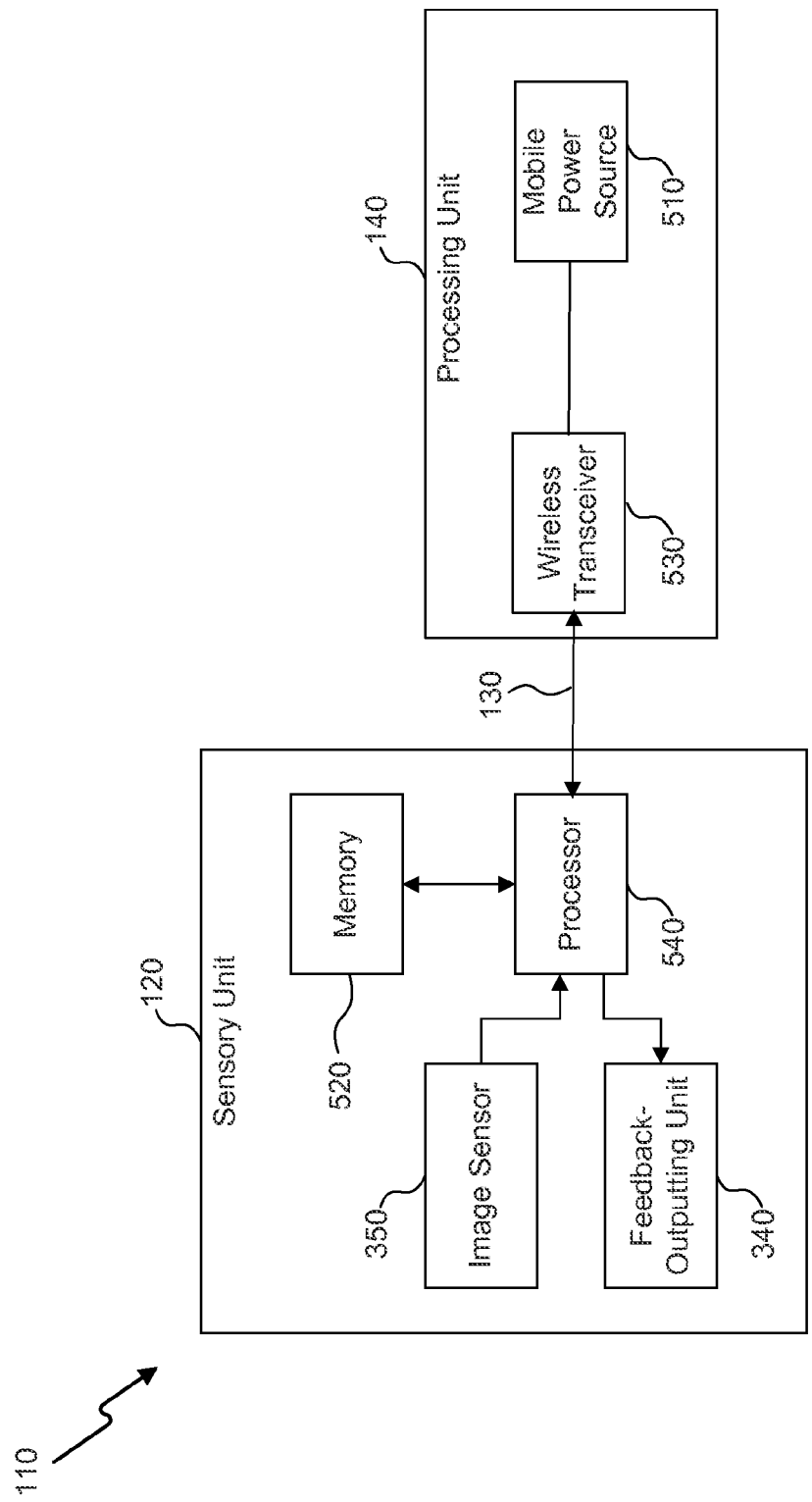
FIG. 5D is a block diagram illustrating an example of the components of an apparatus for aiding persons who have low vision according to a fourth embodiment.

FIG. 5D is a block diagram illustrating the components of apparatus 110 according to a fourth embodiment. In FIG. 5D, sensory unit 120 couples directly to a pair of glasses without the need of a support. In this embodiment, sensory unit 120 includes image sensor 350, feedback-outputting unit 340, processor 540, and memory 520. As shown in FIG. 5D, sensory unit 120 is connected via a wire 130 to processing unit 140. Additionally, in this embodiment, processing unit 140 includes mobile power source 510 and wireless transceiver 530.

As will be appreciated by a person skilled in the art having the benefit of this disclosure, numerous variations and/or modifications may be made to the disclosed embodiments. Not all components are essential for the operation of apparatus 110. Any component may be located in any appropriate part of apparatus 110 and the components may be rearranged into a variety of configurations while providing the functionality of the disclosed embodiments. Therefore, the foregoing configurations are examples and, regardless of the configurations discussed above, apparatus 110 can assist persons who have low vision with their everyday activities in numerous ways.

One way apparatus 110 can assist persons who have low vision is by identifying relevant objects in an environment. For example, in some embodiments, processor 540 may execute one or more computer algorithms and/or signal-processing techniques to find objects relevant to user 100 in image data captured by sensory unit 120. The term "object" refers to any physical object, person, text, or surroundings in an environment.

In one embodiment, apparatus 110 can perform a hierarchical object identification process. In a hierarchical object identification process, apparatus 110 can identify objects from different categories (e.g., spatial guidance, warning of risks, objects to be identified, text to be read, scene identification, and text in the wild) of image data. For example, apparatus 110 can perform a first search in the image data to identify objects from a first category, and after initiating the first search, execute a second search in the image data to identify objects from a second category.

In another embodiment, apparatus 110 can provide information associated with one or more of the objects identified in image data. For example, apparatus 110 can provide information such as the name of an individual standing in front of user 100. The information may be retrieved from a dynamic database stored in memory 520. If the database does not contain specific information associated with the object, apparatus 110 may provide user 100 with nonvisual feedback indicating that a search was made, but the requested information was not found in the database. Alternatively, apparatus 110 may use wireless transceiver 530 to search for and retrieve information associated with the object from a remote database (e.g., over a cellular network or Wi-Fi connection to the Internet).

Another way apparatus 110 can assist persons who have low vision is by performing a continuous action that relates to an object in an environment. A continuous action may involve providing continuous feedback regarding the object. For example, apparatus 110 can provide continuous feedback associated with an object identified within a field-of-view of image sensor 350, and suspend the continuous feedback when the object moves outside the field-of-view of image sensor 350. Examples of continuous feedback may include audibly reading text, playing a media file, etc. In addition, in some embodiments, apparatus 110 may provide continuous feedback to user 100 based on information derived from a discrete image or based on information derived from one or more images captured by sensory unit 120 from the environment of user 100.

Another type of continuous action includes monitoring the state of an object in an environment. For example, in one embodiment, apparatus 110 can track an object as long as the object remains substantially within the field-of-view of image sensor 350. Furthermore, before providing user 100 with feedback, apparatus 110 may determine whether the object is likely to change its state. If apparatus 110 determines that the object is unlikely to change its state, apparatus 110 may provide a first feedback to user 100. For example, if user 100 points to a road sign, apparatus 110 may provide a first feedback that comprises a descriptor of the road sign. However, if apparatus 110 determines that the object is likely to change its state, apparatus 110 may provide a second feedback to user 100 after the object has changed its state. For example, if user 100 points at a traffic light, the first feedback may comprise a descriptor of the current state of the traffic light (e.g., the traffic light is red) and the second feedback may comprise a descriptor indicating that the state of traffic light has changed (i.e., the traffic light is now green).

Apparatus 110 may also determine that an object that is expected to change its state is not functioning and provide appropriate feedback. For example, apparatus 110 may provide a descriptor indicating that a traffic light is broken.

Apparatus 110 can also assist persons who have low vision by making intelligent decisions regarding a person's intentions. Apparatus 110 can make these decisions by understanding the context of a situation. Accordingly, disclosed embodiments may retrieve contextual information from captured image data and adjust the operation of apparatus 110 based on at least the contextual information. The term "contextual information" (or "context") refers to any information having a direct or indirect relationship with an object in an environment. In some embodiments, apparatus 110 may retrieve different types of contextual information from captured image data. One type of contextual information is the time and/or the place that an image of the object was captured. Another example of a type of contextual information is the meaning of text written on the object. Other examples of types of contextual information include the identity of an object, the type of the object, the background of the object, the location of the object in the frame, the physical location of the user relative to the object, etc.

In an embodiment, the type of contextual information that is used to adjust the operation of apparatus 110 may vary based on objects identified in the image data and/or the particular user who wears apparatus 110. For example, when apparatus 110 identifies a package of cookies as an object, apparatus 110 may use the location of the package (i.e., at home or at the grocery store) to determine whether or not to read the list of ingredients aloud. Alternatively, when apparatus 110 identifies a signboard identifying arrival times for trains as an object, the location of the sign may not be relevant, but the time that the image was captured may affect the output. For example, if a train is arriving soon, apparatus 110 may read aloud the information regarding the coming train. Accordingly, apparatus 110 may provide different responses depending on contextual information.

Apparatus 110 may use contextual information to determine a processing action to execute or an image resolution of image sensor 350. For example, after identifying the existence of an object, contextual information may be used to determine if the identity of the object should be announced, if text written on the object should be audibly read, if the state of the object should be monitored, or if an image representation of the object should be saved. In some embodiments, apparatus 110 may monitor a plurality of images and obtain contextual information from specific portions of an environment. For example, motionless portions of an environment may provide background information that can be used to identify moving objects in the foreground.

Yet another way apparatus 110 can assist persons who have low vision is by automatically carrying out processing actions after identifying specific objects and/or hand gestures in the field-of-view of image sensor 350. For example, processor 540 may execute several actions after identifying one or more triggers in image data captured by apparatus 110. The term "trigger" includes any information in the image data that may cause apparatus 110 to execute an action. For example, apparatus 110 may detect as a trigger a finger of user 100 pointing to one or more coins. The detection of this gesture may cause apparatus 110 to calculate a sum of the value of the one or more coins. As another example of a trigger, an appearance of an individual wearing a specific uniform (e.g., a policeman, a fireman, a nurse) in the field-of-view of image sensor 350 may cause apparatus 110 to make an audible indication that this particular individual is nearby.

In some embodiments, the trigger identified in the image data may constitute a hand-related trigger. The term "hand-related trigger" refers to a gesture made by, for example, the user's hand, the user's finger, or any pointed object that user 100 can hold (e.g., a cane, a wand, a stick, a rod, etc.).

In other embodiments, the trigger identified in the image data may include an erratic movement of an object caused by user 100. For example, unusual movement of an object can trigger apparatus 110 to take a picture of the object. In addition, each type of trigger may be associated with a different action. For example, when user 100 points to text, apparatus 110 may audibly read the text. As another example, when user 100 erratically moves an object, apparatus 110 may audibly identify the object or store the representation of that object for later identification.

Apparatus 110 may use the same trigger to execute several actions. For example, when user 100 points to text, apparatus 110 may audibly read the text. As another example, when user 100 points to a traffic light, apparatus 110 may monitor the state of the traffic light. As yet another example, when user 100 points to a branded product, apparatus 110 may audibly identify the branded product. Furthermore, in embodiments in which the same trigger is used for executing several actions, apparatus 110 may determine which action to execute based on contextual information retrieved from the image data. In the examples above, wherein the same trigger (pointing to an object) is used, apparatus 110 may use the type of the object (text, a traffic light, a branded product) to determine which action to execute.

To assist user 100 throughout his or her daily activities, apparatus 100 may follow several procedures for saving processing resources and prolonging battery life. For example, apparatus 110 can use several image resolutions to form images. Higher image resolution provides more detailed images, but requires more processing resources. Lower image resolution provides less detailed images, but saves processing resources. Therefore, to prolong battery life, apparatus 110 may have rules for capturing and processing high resolution image under certain circumstances, and rules for capturing and processing low resolution image when possible. For example, apparatus 110 may capture higher resolution images when performing Optical Character Recognition (OCR), and capture low resolution images when searching for a trigger.

One of the common challenges persons with low vision face on a daily basis is reading. Apparatus 110 can assist persons who have low vision by audibly reading text that is present in user 100 environment. Apparatus 110 may capture an image that includes text using sensory unit 120. After capturing the image, to save resources and to process portions of the text that are relevant to user 100, apparatus 110 may initially perform a layout analysis on the text. The term "layout analysis" refers to any process of identifying regions in an image that includes text. For example, layout analysis may detect paragraphs, blocks, zones, logos, titles, captions, footnotes, etc.

In one embodiment, apparatus 110 can select which parts of the image to process, thereby saving processing resources and battery life. For example, apparatus 110 can perform a layout analysis on image data taken at a resolution of one megapixel to identify specific areas of interest within the text. Subsequently, apparatus 110 can instruct image sensor 350 to capture image data at a resolution of five megapixels to recognize the text in the identified areas. In other embodiments, the layout analysis may include initiating at least a partial OCR process on the text.

In another embodiment, apparatus 110 may detect a trigger that identifies a portion of text that is located a distance from a level break in the text. A level break in the text represents any discontinuity of the text (e.g., a beginning of a sentence, a beginning of a paragraph, a beginning of a page, etc.). Detecting this trigger may cause apparatus 110 to read the text aloud from the level break associated with the trigger. For example, user 100 can point to a specific paragraph in a newspaper and apparatus 110 may audibly read the text from the beginning of the paragraph instead of from the beginning of the page.

In addition, apparatus 110 may identify contextual information associated with text and cause the audible presentation of one portion of the text and exclude other portions of the text. For example, when pointing to a food product, apparatus 110 may audibly identify the calorie value of the food product. In other embodiments, contextual information may enable apparatus 110 to construct a specific feedback based on at least data stored in memory 520. For example, the specific feedback may assist user 100 to fill out a form (e.g., by providing user 100 audible instructions and details relevant to a form in the user's field-of-view).

To improve the audible reading capabilities of apparatus 110, processor 540 may use OCR techniques. The term "optical character recognition" includes any method executable by a processor to retrieve machine-editable text from images of text, pictures, graphics, etc. OCR techniques and other document recognition technology typically use a pattern matching process to compare the parts of an image to sample characters on a pixel-by-pixel basis. This process, however, does not work well when encountering new fonts, and when the image is not sharp. Accordingly, apparatus 110 may use an OCR technique that compares a plurality of sets of image regions that are proximate to each other. Apparatus 110 may recognize characters in the image based on statistics relate to the plurality of the sets of image regions. By using the statistics of the plurality of sets of image regions, apparatus 110 can recognize small font characters defined by more than four pixels e.g., six or more pixels. In addition, apparatus 110 may use several images from different perspectives to recognize text on a curved surface. In another embodiment, apparatus 110 can identify in image data an existence of printed information associated with a system command stored in a database and execute the system command thereafter. Examples of a system command include: "enter training mode," "enter airplane mode," "backup content," "update operating system," etc.

The disclosed OCR techniques may be implemented on various devices and systems and are not limited to use with apparatus 110. For example, the disclosed OCR techniques provide accelerated machine reading of text. In one embodiment, a system is provided for audibly presenting a first part of a text from an image, while recognizing a subsequent part of the text. Accordingly, the subsequent part may be presented immediately upon completion of the presentation of the first part, resulting in a continuous audible presentation of standard text in less than two seconds after initiating OCR.

As is evident from the foregoing, apparatus 110 may provide a wide range of functionality. More specifically, embodiments consistent with the present disclosure may provide an apparatus, a method, and a software product stored on a non-transitory computer readable medium for recognizing text on a curved surface.

Figure 6:
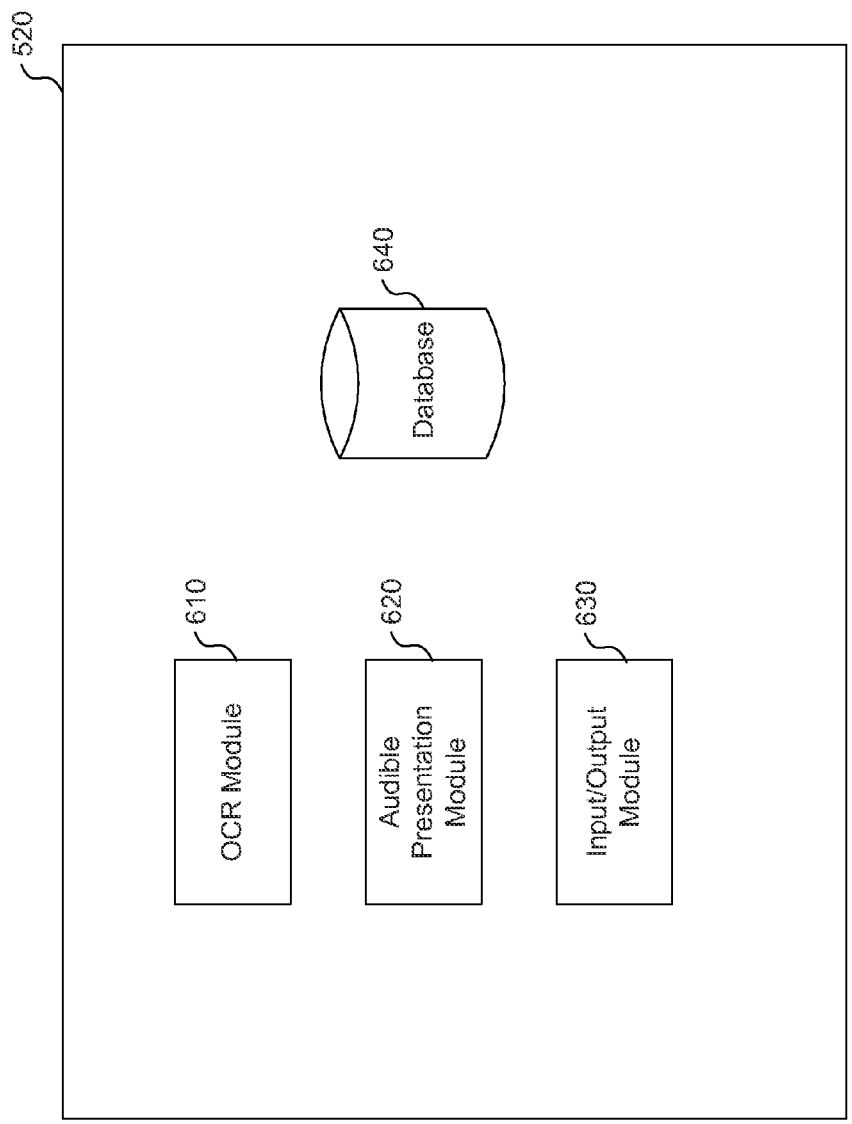
FIG. 6 is a block diagram illustrating an example of a memory storing software modules.

In some embodiments, recognizing text on a curved surface may be implemented using apparatus 110 with software instructions loaded into memory 520. The software instructions, when executed by processor 540, may perform various functions related to text recognition. FIG. 6 is a block diagram illustrating an example of a set of software instructions, organized in different functional modules, which can be loaded into memory 520 for recognizing text on a curved surface.

Referring to FIG. 6, memory 520 may store an OCR module 610, which may include software instructions for perform OCR processing. OCR module 610 can generate a recognized representation of a text based on an image that includes the text. The recognized representation of the text may include a collection of letters, words, phrases, sentences, or any other suitable semantic symbols. In some embodiments, the recognized representation of the text may include audible reading of the text. The image containing the text may include a static image, a frame of a video stream, or any other graphical forms that contain at least a part of the text.

Memory 520 may store an audible presentation module 620, which may include software instructions for performing an audible presentation, such as reading aloud, of the recognized representation of the text generated by the OCR module 610. Audible presentation module 620 may execute the software instructions to perform an audible presentation after at least a part of the text has been recognized by OCR module 610. In some embodiments, audible presentation module 620 may simultaneously perform an audible presentation of the first part of the text while OCR module 610 is recognizing the second part of the text.

Memory 520 may store an input/output (I/O) module 630, which may include software instructions for performing image capture, audio output, user selection, or similar functions. For example, I/O module 630 may perform image capture from image sensor 350. In another example, I/O module 630 may perform audible feedback through feedback-outputting unit 340.

Memory 520 may store a database 640. Database 640 may contain data related to OCR, audible presentation, and/or input/output functions. For example, database 640 may store data of images or frames captured by image sensor 350 to be recognized by OCR module 610. Database 640 may store recognized representation generated by OCR module 610. Database 640 may store audible data to be presented to the user through feedback-outputting unit 340. Other forms of data related to the functions performed by modules 610, 620, and 630, including transitional or temporary data, may also be stored in database 640.

In other embodiments, database 640 may be located remotely from memory 520, and be accessible to other components of apparatus 110 (e.g., processing unit 140) via one or more wireless connections (e.g., a wireless network). While one database is shown, it should be understood that several separate and/or interconnected databases may make up database 640. Database 640 may include computing components (e.g., database management system, database server, etc.) configured to receive and process requests for data stored in memory devices associated with database 640 and to provide data from database 640.

OCR module 610, audible presentation module 620, and input/output module 630 may be implemented in software, hardware, firmware, a mix of any of those, or the like. For example, if the modules are implemented in software, they may be stored in memory 520, as shown in FIG. 6. Other components of processing unit 140 and/or sensory unit 120 may be configured to perform processes to implement and facilitate operations of the modules. Thus, OCR module 610, audible presentation module 620, and input/output module 630 may include software, hardware, or firmware instructions (or a combination thereof) executable by one or more processors (e.g., processor 540), alone or in various combinations with each other. For example, OCR module 610, audible presentation module 620, and input/output module 630 may be configured to interact with each other and/or other modules of apparatus 110 to perform functions consistent with disclosed embodiments. In some embodiments, any of the disclosed modules (e.g., OCR module 610, audible presentation module 620, and input/output module 630) may each include dedicated sensors (e.g., IR, image sensors, etc.) and/or dedicated application processing devices to perform the functionality associated with each module.

Figure 7:
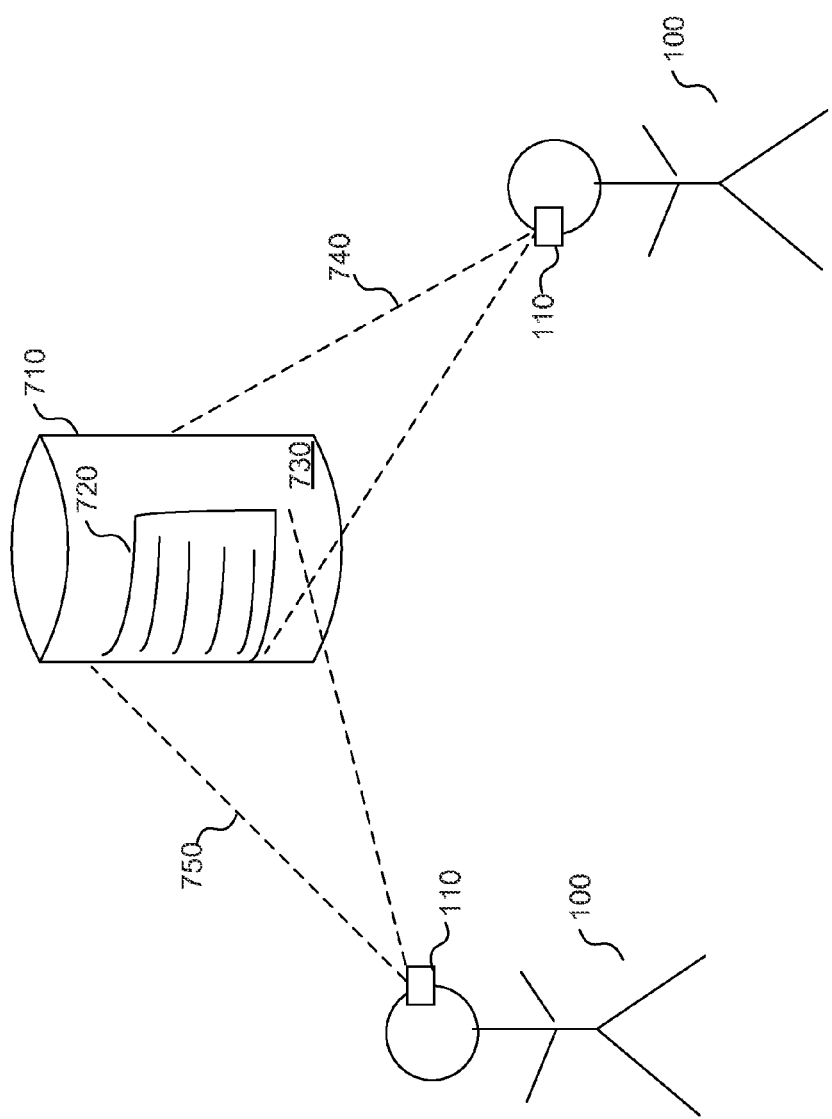
FIG. 7 is a schematic illustration of an example of a user using an apparatus to recognize text on a curved surface from two perspectives.

FIG. 7 is a schematic illustration of an example of a user 100 using apparatus 110 to recognize text 720 on a curve surface 730 from two perspectives. In FIG. 7, an object 710 has curved surface 730. As used herein, a curved surface includes any surface containing at least one bend, arc, round, or any other non-straight structure. For example, the outer surfaces of a bottle, a can, a tin, and a cathode ray tube (CRT) screen are all examples of a curved surface. For simplicity, an object having a curved surface is herein referred to as a curved object. Referring back to FIG. 7, curved object 710 may include a display of an electric device, such as a television screen or a computer monitor, and text 720 may include text shown on the display. In other embodiments, curved object 710 may include a food product (e.g., a food product with a can or a tin package), a beverage (e.g., a bottle or a can), a pharmaceutical drug (e.g., a drug with a drug bottle), etc., and text 720 may include text on a label associated with curved object 710.

As shown in FIG. 7, user 100 may be equipped with apparatus 110. As described above, apparatus 110 may include image sensor 350. Image sensor 350 may be connected to glasses 105 worn by user 100, to enable image sensor 350 to move with the head of user 100. Image sensor 350 may be configured to be movable with the head of user 100 in such a manner that an aiming direction of image sensor 350 substantially coincides with a field of view of user 100. For example, as described above, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

Apparatus 110 may capture images of different perspectives of text 720. As used herein, a perspective of text may include the text viewed from a certain angle, an image of the text having a certain resolution, a frame in a video stream of the text, or other forms of graphical representation of the text.

For example, user 100 may use apparatus 110 to capture a first image of text 720 at a first position (right hand side) or at a first angle towards curved object 710, with a field of view 740 covering a first portion of curved surface 730. The first image contains a first perspective of text 720. User 100 may also use apparatus 100 to capture a second image of text 720 at a second position (left hand side) or at a second angle towards curved object 710, with a field of view 750 covering a second portion of curved surface 730. The second image contains a second perspective of text 720. It is noted that when capturing images of text 720, user 100 may also slightly move her head to change the coverage or direction of her field of view, without physically moving her body from one position to another position.

In another example, user 100 may use apparatus 110 to capture a video stream while moving from the first position to the second position (or moving from the first angle to the second angle towards curved object 710). As used herein, a video stream may include a series of pictures collectively forming a motion picture of a scene. Each picture in the video stream may also be referred to as a frame. In some embodiments, each frame may contain image data with full resolution (e.g., in case of progressive scan). In other embodiments, each frame may contain image data with half resolution (e.g., in case of interlaced scan). Regardless of which scanning technique is used, user 100 may capture a video stream of text 720, which includes multiple frames of text 720 captured at different time. Each frame of the captured video stream contains one perspective of text 720. It is noted that when capturing a video stream, user 100 may also slightly move her head to change the coverage or direction of her field of view, without physically moving from one position to another position.

In yet another example, user 100 may stay substantially stationary when capturing images or video stream, e.g., without substantially changing the coverage or direction of her field of view, but capture images or video stream of text 720 with different resolutions. As used herein, a resolution of an image or a video stream may be defined by the number of pixels composing the image or the video stream. For example, an image may have a resolution of 800×600, 1024×768, etc. A video stream may have a resolution of 640×480, 1280×720, 1920×1080, etc. (each resolution may also contain variations of progressive scan, such as 480p, 720p, 1080p; and interlaced scan, such as 480i, 720i, 1080i). For video streams, teams such as standard resolution (or "SD", e.g., 480i and 480p), high resolution (or "HD", e.g., 720i/720p, 1080i/1080p, etc.), and ultra-high resolution (or UHD, e.g., 4K resolution: 3840×2160 or other variations having horizontal pixel count on the order of 4000) are also used to define resolution. Resolution can also be defined by the total number of pixels of an image sensor used to product an image or a video stream. For example, an image or a video stream may have a resolution of 3 M, 5 M, 8 M, 16 M, 27 M, etc., where "M" refers to megapixels. Resolution may also be defined by pixel density, such as dots per inch (DPI), pixels per inch (PPI), lines per inch (LPI), pixels per centimeter, etc. For example, an image or a video stream may have a resolution of 120 DPI, 160 DPI, 240 DPI, 320 DPI, 480 DPI, 640 DPI, etc.

Referring back to FIG. 7, user 100 may capture multiple images, multiple video streams, or a video steam with multiple frames, where the multiple images/video streams/frames have different resolutions. User 100 may conduct the image/video capture without substantially changing the coverage or direction of her field of view. For example, user 100 may capture multiple images having different resolutions with her field of view 740 substantially unchanged. A first image having a first resolution contains a first perspective of text 720. A second image having a second resolution contains a second perspective of text 720. In another example, user 100 may capture multiple video streams having different resolutions. A first video stream having a first resolution contains a first perspective of text 720. A second video stream having a second resolution contains a second perspective of text 720. In yet another example, user 100 may capture one video stream contains multiple frames, where the multiple frames have different resolutions. A first frame having a first resolution contains a first perspective of text 720. A second frame having a second resolution contains a second perspective of text 720.

Figure 8C:
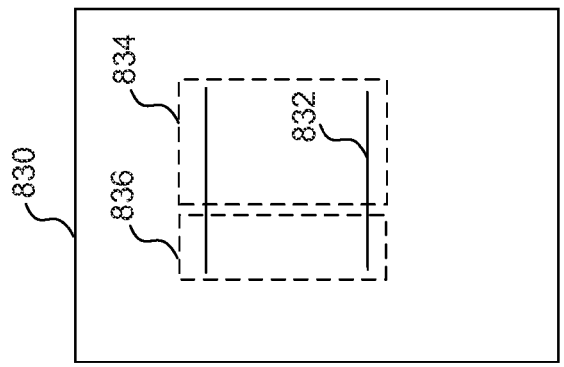
FIGS. 8A-8C are schematic illustrations of examples of text viewed from different perspectives.
Figure 8B:
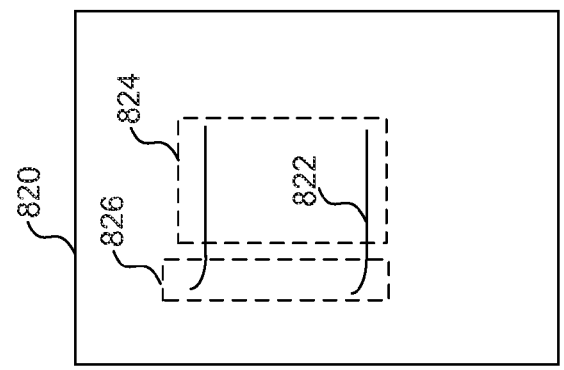
Figure 8A:
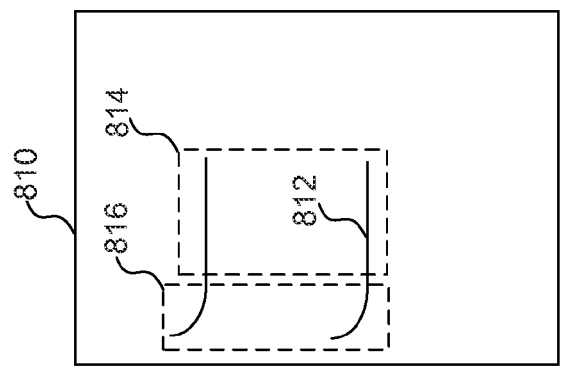

FIGS. 8A-8C are schematic illustrations of examples of text from different perspectives. FIG. 8A shows an image or frame 810 (herein after image 810 for simplicity) captured when, for example, user 100 is at the first position (e.g., the right hand side in FIG. 7) with field of view 740. In image 810, text 720 on curved surface 730 is captured as text section 812. Text section 812 may constitute a first perspective of text 720. Because of the limited coverage of field of view 740 and/or the nature of curved surface 730, a portion of text section 812, for example portion 816, is unrecognizable in an OCR process. For example, portion 816 may contain skewed text. Text section 812 may also contain a portion of text, for example portion 814, which can be recognized in an OCR process.

FIG. 8B shows an image or frame 820 (herein after image 820 for simplicity) captured when, for example, user 100 is at a position (not shown in FIG. 7) between the first (right hand side in FIG. 7) and second (left hand side in FIG. 7) positions. In this intermediate position, text 720 on curved surface 730 is captured as text section 822. As user 100 moves to the left, her field of view may align better with text 720. As a result, text section 822 may shift towards the center of image 820 and a portion of text unrecognizable by an OCR process, such as portion 826, may become smaller. Accordingly, a portion of text that can be recognized by an OCR process, such as portion 824, becomes larger.

FIG. 8C shows an image or frame 830 (herein after image 830 for simplicity) captured when, for example, user 100 is at the second position (e.g., the left hand side in FIG. 7) with field of view 750. In the second position, text 720 on curved surface 730 is captured as text section 832. Text section 832 may constitute a second perspective of text 720. When the user moves to the second position, her field of view 750 may cover the entire portion of text 720 and may align with text 720. As a result, text section 832 may further shift towards the center of image 830. Previously unrecognizable portion 816 in image 810 may now become recognizable portion 836. In other words, while portion 816 and 836 correspond to substantially the same portion of text in text 720, in image 810 portion 816 is not recognizable due to, for example, skewed text, but in image 830 portion 836 is recognizable because the text is no longer skewed when captured from field of view 750. Image 830 may also contain a portion 834 corresponding to other portion of text 720 captured in image 830.

In some embodiments, when FIGS. 8A-8C represents frames of a video stream, frame 820 may be captured subsequent to frame 810, and frame 830 may be captured subsequent to frame 820. In one example, frames 810, 820, and 830 may be captured consecutively. In an OCR process, frame 830, rather than frame 820, may be used to recognize text portion 836 that is unrecognizable in portion 816.

Figure 9B:
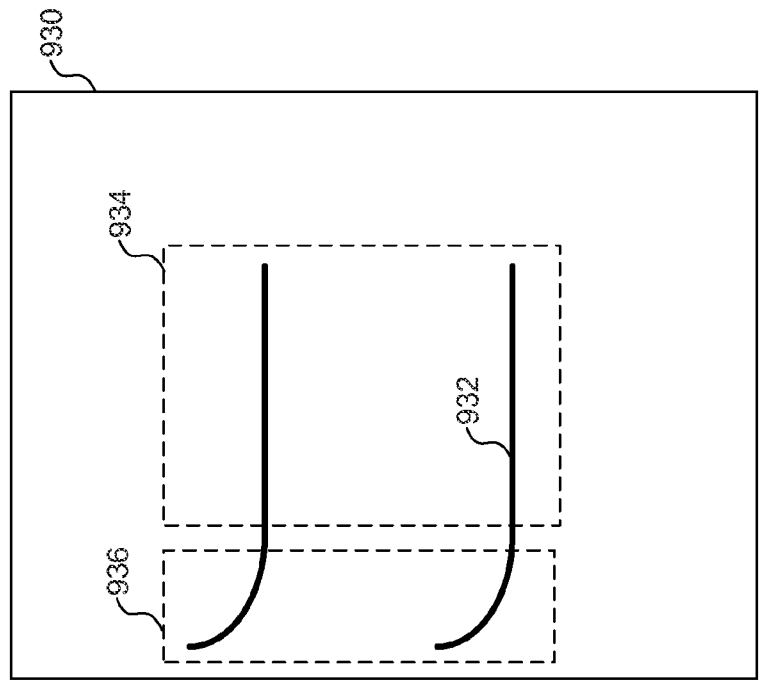
FIGS. 9A-9B are schematic illustrations of additional examples of text viewed from different perspectives.
Figure 9A:
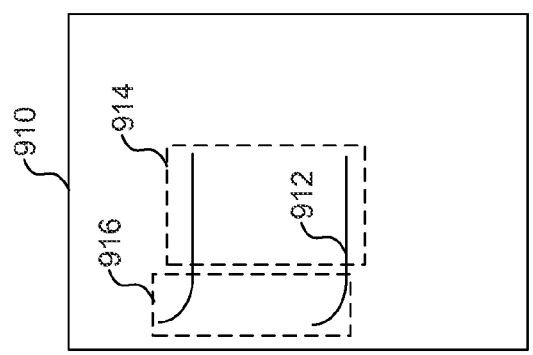

FIGS. 9A and 9B are schematic illustrations of additional examples of text viewed from different perspectives. FIG. 9A is similar to FIG. 8A, showing an image or frame 910 (herein after image 910 for simplicity) captured when, for example, user 100 is at the first position (e.g., the right hand side in FIG. 7) with field of view 740. In image 910, text 720 on curved surface 730 is captured as text section 912. Text section 912 may constitute a first perspective of text 720. Because of the limited coverage of field of view 740 and/or the nature of curved surface 730, a portion of text section 912, for example portion 916, is unrecognizable in an OCR process. For example, portion 916 may contain skewed text. Text section 912 may also contain a portion of text, for example portion 914, which can be recognized in an OCR process.

FIG. 9B shows an image or frame 930 (herein after image 910 for simplicity) captured with a higher resolution. User 100 may or may not need to move to a new position or change her field of view to capture image 930. Image 930 contains more pixels than image 910. Therefore, image 930 is shown in FIG. 9B in a larger size assuming the pixel density is unchanged. Alternatively, image 930 may also be shown in the same size as image 910 but with a higher pixel density. Text section 932 may constitute a second perspective of text 720. Because of the increased pixel count, previously unrecognizable portion 916 may now become recognizable portion 936. Image 930 may also contain a portion 934 corresponding to other portion of text 720 captured in image 930.

Figure 10:
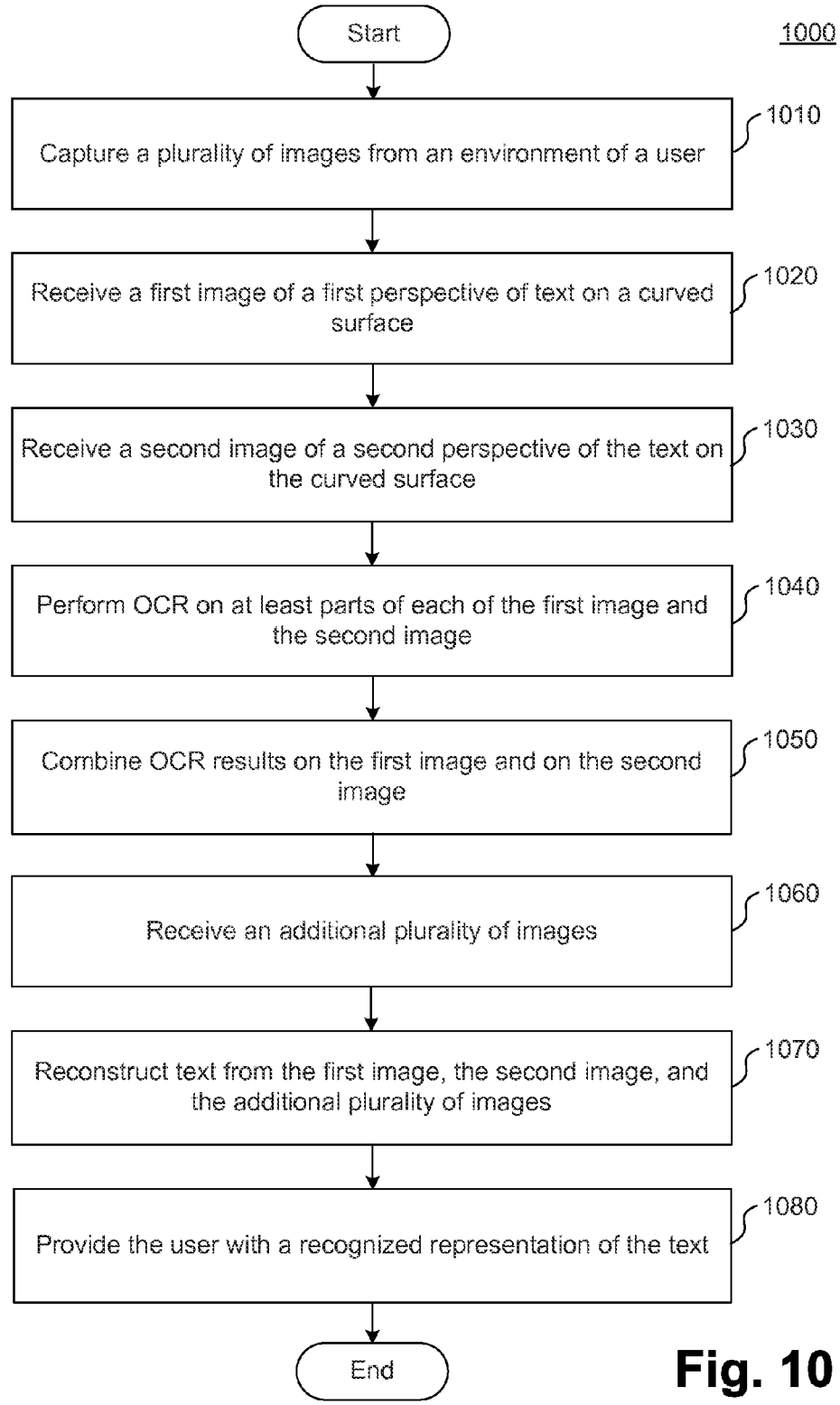
FIG. 10 is a flow chart of an exemplary process for recognizing text on a curved surface.

In some embodiments, apparatus 110 may be used to recognize text on a curved surface. FIG. 10 is a flow chart of an exemplary process 1000 performed by apparatus 110 to implement text recognition. For example, apparatus 110 may include at least one processor device (e.g., processor 540) to execute one or more steps of process 1000. It is noted that process 1000 may be executed before or after another process, or can be embedded into other processes.

Apparatus 100 may comprise an image sensor such as image sensor 350. In step 1010, image sensor 350 may capture from an environment of user 100 a plurality of images (e.g., images 810, 820, 830 or images 910 and 930) of text (e.g., text 720) on a curved surface (e.g., surface 730). The environment may include object 710 having the curved surface 730. The captured images may be saved in memory 520 (e.g., in database 640).

In step 1020, processor 540 may receive a first image (e.g., image 810) of a first perspective of text (e.g., text section 812) on the curved surface. The first image may include a first portion of text unrecognizable in an optical character recognition process. For example, processor 540 may receive the first image 810 by executing program instructions stored in I/O module 630 to retrieve image 810 captured by image sensor 350 and saved in database 640. Text section 812 may include a portion 816 that is unrecognizable in an OCR process due to, for example, skewed text caused by limited coverage of field of view and/or curved surface 730.

In step 1030, processor 540 may receive a second image (e.g., image 830) of a second perspective of the text (e.g., text section 832) on the curved surface. The second image may include the first portion of text in a form capable of recognition in the optical character recognition process. For example, text section 832 may include portion 836 that is capable of recognition in an OCR process.

In step 1040, processor 540 may perform optical character recognition on at least parts of each of the first image and the second image. For example, processor 540 may execute program instructions stored in OCR module 610 to perform the OCR process. Processor 540 may perform OCR on text portion 814 (e.g., recognizable) of the first image 810 and text portion 836 (e.g., recognizable) of the second image 830.

In step 1050, processor 540 may combine results of the optical character recognition of the first image and the second image. For example, processor 540 may combine the OCR results of text portion 814 in the first image 810 and text portion 836 in the second image 830 to form a combined OCR result of text 720 on curved surface 730. Text portions 816 and 834 may collectively cover the content of text 720.

In some cases, the combination of text portions 816 and 834 may not cover the entire content of text 720 or the combined OCR results may not be satisfactory. In such cases, apparatus 110 may perform an OCR sub process to reconstruct text on the curved surface based on additional images (e.g., images in addition to images 810 and 830). Steps 1060 and 1070 show an example of such sub process.

In step 1060, processor 540 may receive an additional plurality of images. For example, processor 540 may execute program instructions stored in I/O module 630 to receive a plurality of images in addition to images 810 and 830. The additional plurality of images may be captured by image sensor 350 before, between, or after images 810 and 830 are captured. For example, user 100 may use apparatus 110 to capture a series of images while moving around curved object 710, and two of the series of images may be used to perform initial OCR to reconstruct text on curved surface 730, as described in steps 1020-1050. When additional images are needed, processor 540 may choose the additional images from the rest of the series of images, and images captured before, between, or after images 810 and 830 may be chosen as candidates. In another example, when additional images are needed, processor 540 may prompt user 100 to capture additional images of, for example, different perspectives from those of previously captured.

In step 1070, processor 540 may perform OCR on the additional images to reconstruct text from the first image (e.g., image 810), the second image (e.g., image 830), and the additional plurality of images. For example, processor may perform OCR on the additional images and combine the OCR results of the additional images with the OCR results of images 810 and 830. In this case, OCR is performed on individual images and the OCR results are combined afterwards. In another example, the image data of one or more images may be combined first and OCR process may be performed on the combined image data. These two approaches will be described in greater detail later with respect to FIGS. 11 and 12.

In step 1080, processor 540 may provide user 100 with a recognized representation of the text, including a recognized representation of the first portion of text. For example, processor 540 may execute program instructions stored in audible presentation module 620 to perform audible reading of recognized text (e.g., combined text portions 816 and 834 or the reconstructed text from image 810, image 830, and additional images generated in step 1070 if the results of step 1050 is not satisfactory) to user 100.

The above description of process 1000 is described in connection with the exemplary images shown in FIGS. 8A and 8C. It is noted that process 1000 may also be implemented using other images. For example, the first and second images may be images 910 and 930 shown in FIGS. 9A and 9B, respectively. Accordingly, the first perspective of text may be text section 912, and the second perspective of text may be text section 932. As described above, image 930 has a higher resolution than image 910. Therefore, even if images 910 and 930 are captured with substantially the same field of view (e.g., direction and/or coverage), text portion 936 may be recognizable while text portion 916 is not. By combining recognizable portion 914 in image 910 and recognizable portion 936 in image 930, processor 540 may reconstruct text 720 on curved surface 730 for audible presentation to user 100.

In some embodiments, process 1000 may be implemented based on a video stream instead of, or in addition to, static images. When process 1000 is implemented based on a video stream, the first and second images may be first and second frames of the video stream. Steps to recognize and combine video frames are similar to those for processing static images, as discussed above.

Figure 11:
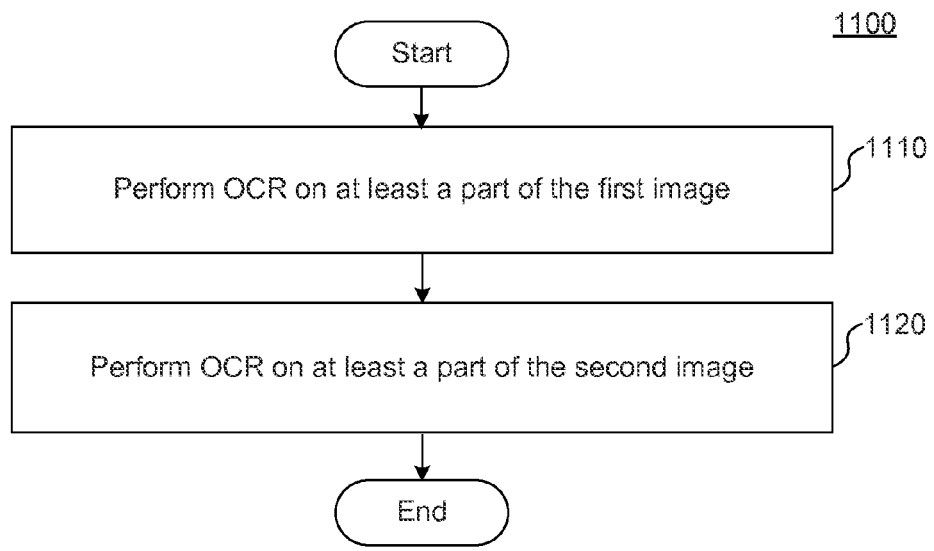
FIG. 11 is a flow chart of an exemplary process for performing optical character recognition.
Figure 12:
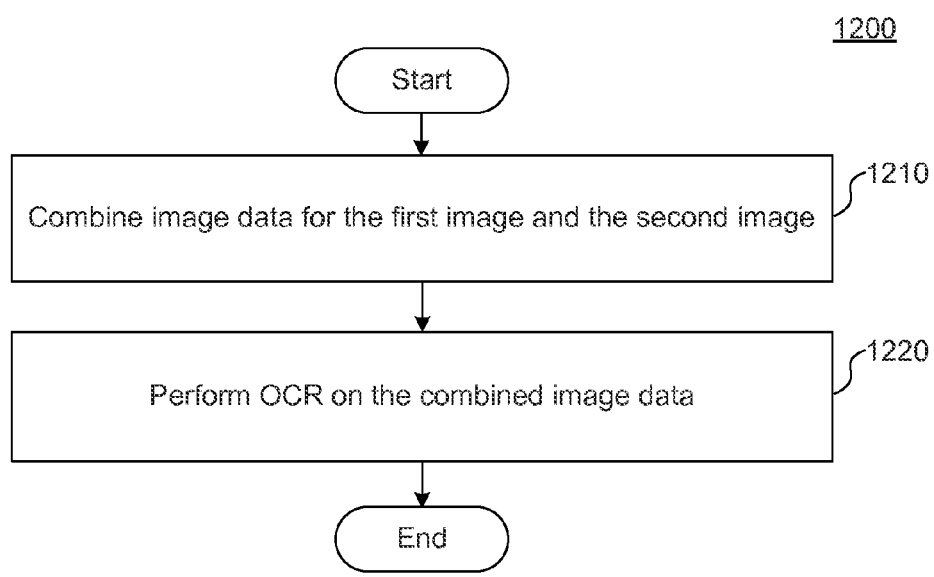
FIG. 12 is a flow chart of another exemplary process for performing optical character recognition.

Different approaches can be adopted to recognize and combine text images. FIGS. 11 and 12 show two exemplary processes 1100 and 1200, respectively, to perform the OCR step (e.g., step 1040 in FIG. 10) and/or combination step (e.g., step 1050 in FIG. 10).

FIG. 11 shows an exemplary process 1100 for performing OCR on the first and second images, which may be a sub process of step 1040 in FIG. 10. In process 1100, processor 540 performs OCR separately on the first image and the second image. For example, in step 1110, processor 540 performs OCR on at least a part of the first image, e.g., portion 814 of image 810. In step 1120, processor 540 separately performs OCR on at least a part of the second image, e.g., portion 834 of image 830. After the parts of the first and second images are separately recognized, processor 540 may continue the process according to step 1050 in FIG. 10 to combine the OCR results.

FIG. 12 shows another exemplary process 1200 for performing OCR on the first and second images. In process 1200, processor 540 first combines image data for the first image and the second image and, thereafter, performs OCR on the combined image data. For example, in step 1210, processor 540 may combine image data of portion 814 of image 810 and portion 836 of image 830 to form a combined image. Then, in step 1220, processor 540 may perform OCR on the combined image data to recognize text.

Figure 13:
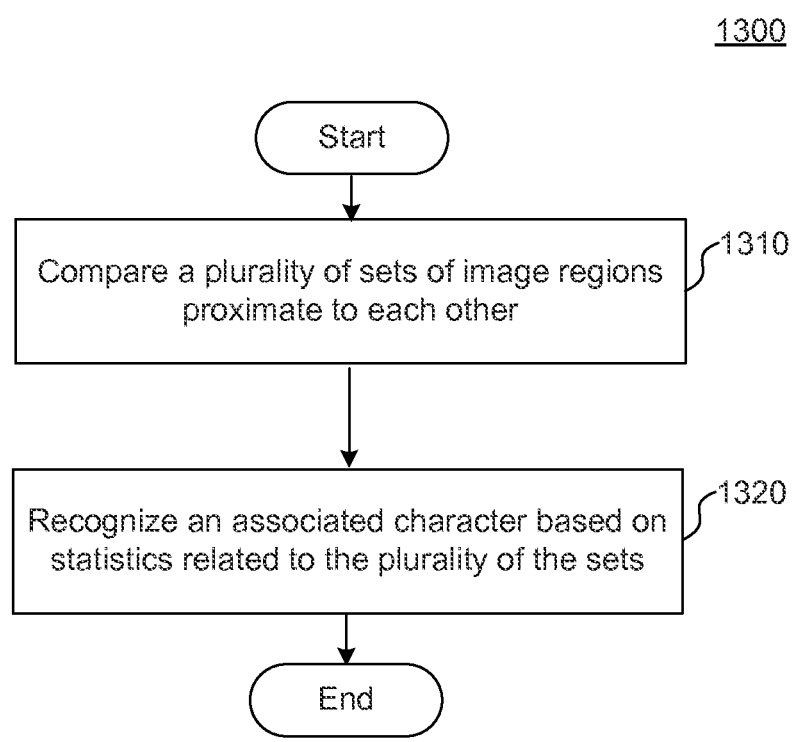
FIG. 13 is a flow chart of yet another exemplary process for performing optical character recognition.

FIG. 13 shows an exemplary process 1300 for performing OCR. Process 1300 may be a sub process of step 1040 in FIG. 10. In step 1310, processor 540 may compare a plurality of sets of image regions that are proximate to each other. For example, processor 540 may compare text regions of image to be recognized with a set of candidate image regions that have already been associated with text characters or representations. The candidate image regions and associated text characters or representations may be stored, for example, in database 640. The comparison may yield likelihoods that the to-be-recognized image regions match one or more candidate image regions that have already established text association. In step 1320, processor 540 may recognize an associated character based on statistics related to the plurality of sets of image regions. For example, processor 540 may recognize a text character based on statistical results, e.g., the likelihoods of matching between the to-be-recognized image regions and the candidate image regions.

Figure 14:
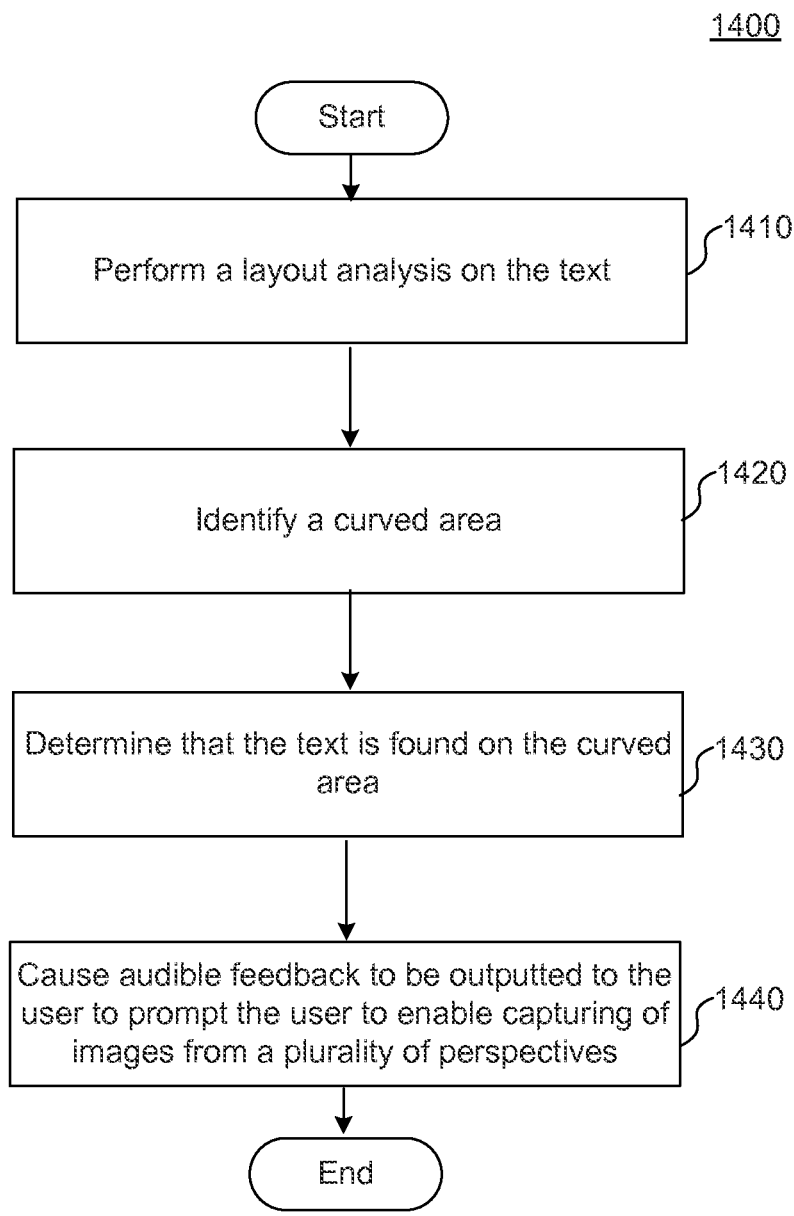
FIG. 14 is a flow chart of an exemplary process for identifying a curved area and determining whether text is found on the curved area.

In some embodiments, apparatus 110 may identify a curved area and/or determine that text if found on a curved area before performing image capture/recognition using different perspectives. FIG. 14 shows an exemplary process 1400 for identifying a curved area and determining whether text is found on the curved area. It is noted that process 1400 may be performed before step 1010 or before step 1020 in FIG. 10. Process 1400 may be initiated when one or more text images are captured by apparatus 110 (e.g., using image sensor 350). In step 1410, processor 540 may perform a layout analysis on the text. For example, after image 810 is captured, processor 540 may analyze the layout of text section 812, such as starting/ending point, start/end of a line, line direction, change of line direction, etc. In step 1420, processor 540 may identify one or more curved areas based on the layout analysis. For example, processor 540 may identify area 816 as a curved area base on, for example, the direction of text lines changes beyond a threshold. Other criteria may also be used to identify curved areas.

In some embodiments, processor 540 may identify a curved area using other methods. For example, processor 540 may analyze the shade pattern, light distribution, image distortion, of other characteristics of an image to identify a curved area. After a curved area is identified, process 1400 may proceed to step 1430 to determine whether text is found in the curved area. For example, processor 540 determine that text is found in the curved area if the curved area contains any shape resembling text characters (e.g., even skewed characters), or if the curved area is close to any non-curved area that contains text, or by other suitable means. Once processor 540 determines that text is found in a curved area, or identifies that a text area is curved, process 1400 may proceed to step 1440. In step 1440, processor 540 may cause audible feedback to be outputted to user 100 to prompt user 100 to enable capturing of images from a plurality of perspectives. For example, processor 540 may execute program instructions stored in I/O module 630 to output audible feedback to user 100 to instruct user 100 to capture images using higher resolution, from different angles, with different field of views, etc.

Figure 15:
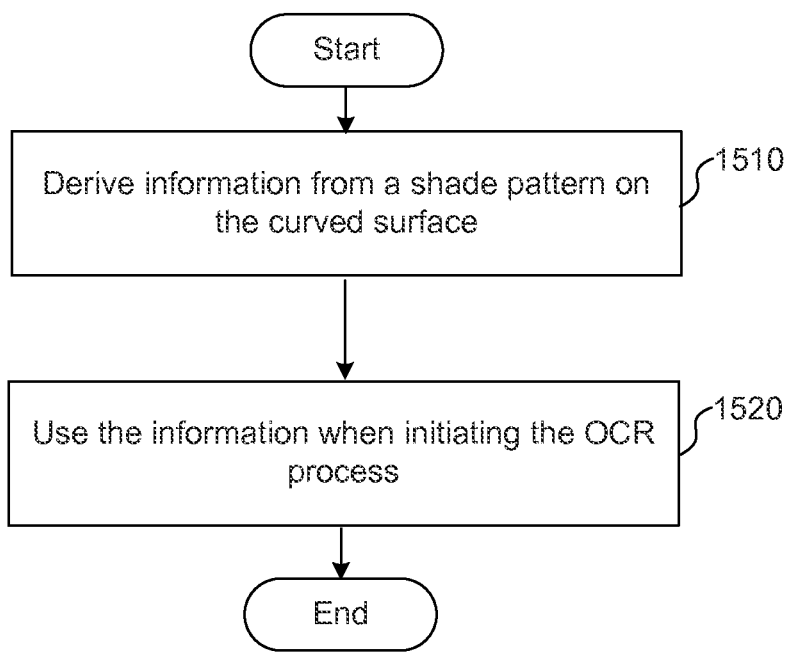
FIG. 15 is a flow chart of an exemplary process for performing optical character recognition.

In some embodiments, information other than text in a curved area may be used to perform an OCR process. FIG. 15 shows a process 1500 for performing OCR using information derived from a shade pattern. Process 1500 may be a sub process of step 1040 in FIG. 10. In step 1510, processor 540 may derive information from a shade pattern on a curved surface. For example, processor 540 may analyze the shade pattern on surface 730 or from image 810. Due to the curvature of surface 730, certain areas of surface 730 may exhibit a different shade pattern (e.g., the image may be darker at the curved areas). In step 1520, processor 540 may use the derived information when initiating the optical character recognition. For example, processor 540 may use the derived information to aid the OCR process. In some embodiments, processor 540 may identify a curved area based on the shade pattern information. In other embodiments, processor 540 may perform image enhancement on the image based on the shad pattern information, e.g., brightening the darker areas such that text in these darker areas are easier to recognize.

Figure 16:
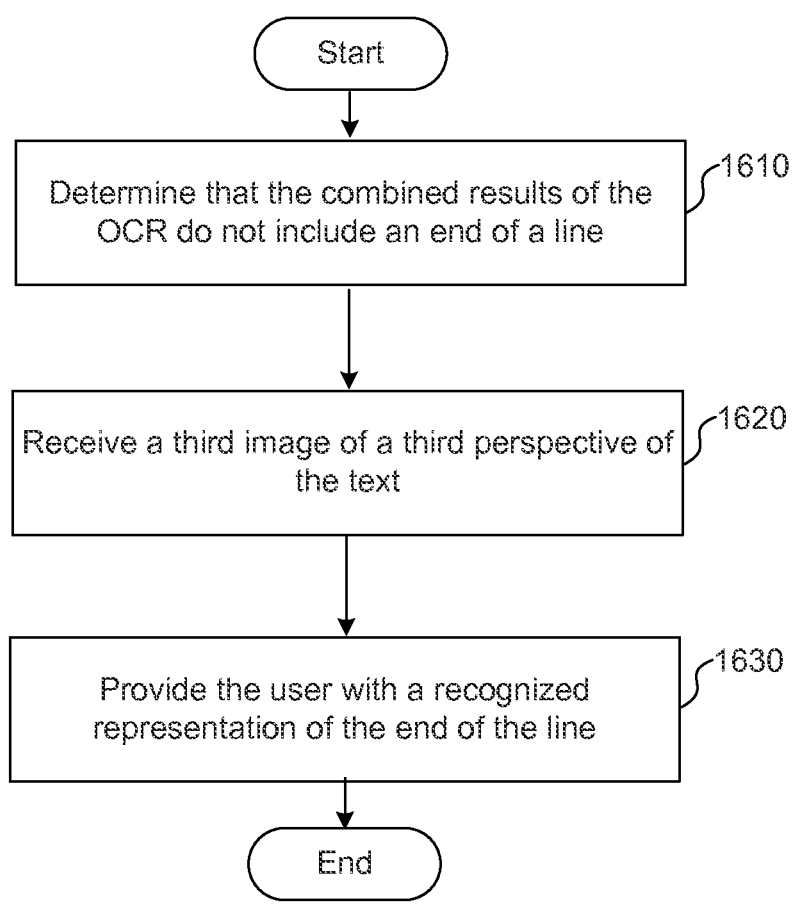
FIG. 16 is a flow chart of an exemplary process for providing a user with a recognized representation of an end of line.

FIG. 16 shows a process 1600 for providing user 100 with a recognized representation (e.g., an audible reading) of an end of a line. An end of line may include an end of a sentence, an end of a row/column of text, an end of a passage or paragraph, an end of a page, etc. To provide user 100 with an audible reading of an end of line may help user 100 to realize that a certain section of text (e.g., a sentence, a row or column, a passage or paragraph, a page, etc.) has been recognized and presented. Examples of recognized representations of an end of line may include a termination phrase such as "end," "over," "finished," "completed," etc.; an audible tone; a short period of stop or silence; a vibration; or other recognizable forms of notification.

Process 1600 may be performed after step 1080 in FIG. 10. In step 1610, processor 540 may determine that the combined results of the optical character recognition process (e.g., combined OCR results from step 1050 or results from step 1070 that takes into account information from additional images) do not include an end of a line. For example, text sections 812 and 832 may not cover an entire sentence, row/column, passage/paragraph, etc. Processor 540 may determine such a situation exists through, for example, analyzing the layout, punctuation, etc. of the text. In step 1620, processor 540 may receive a third image (e.g., a different image from the first and second images received in steps 1020 and 1030) of a third perspective of the text (e.g., a different perspective from the first and second perspectives described in steps 1020 and 1030). For example, processor 540 may instruct user 100 to take one or more additional images having a different perspective (e.g., the one or more additional images cover the end of line of the text) from those of images 810 and 830 and save the one or more additional images in memory 520 (e.g., database 640). These additional images may be retrieved by processor 540 from memory 520 to recognize the text portion related to the end of the line. In step 1630, processor 540 may provide user 100 with a recognized representation of the end of the line. For example, processor 540 may provide user 100 with audible reading of a termination phrase, an audible tone; a short period of stop or silence; a vibration; or other recognizable forms of notification, as described above.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks, floppy disks, or CD ROM, or other forms of RAM or ROM, USB media, DVD, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets. One or more of such software sections or modules can be integrated into a computer system or existing e-mail or browser software.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. An apparatus for recognizing text on a surface, the apparatus comprising:
    an image sensor configured to capture images from an environment of a user; and
    at least one processor device configured to:
        identify the surface is a curved surface based on at least one of the images;
        determine that text is found on the identified curved surface;
        receive a first image of a first perspective of text on the curved surface, wherein the first image includes a first portion of text on the curved surface, the first portion of text including skewed characters that are unrecognizable in an optical character recognition process due to a curvature of the first portion of text on the curved surface viewed from the first perspective, and wherein the first image includes a second portion of text recognizable in the optical character recognition process;
        receive a second image of a second perspective of the text on the curved surface, wherein the second image includes the first portion of text in a form capable of recognition in the optical character recognition process;
        perform optical character recognition on the second portion of text in the first image and the first portion of text in the second image;
        combine results of the optical character recognition on the second portion of text in the first image and on the first portion of text in the second image; and
        provide the user with a recognized representation of the text, including a recognized representation of the second portion of text in the first image and the first portion of text in the second image.

2. The apparatus of claim 1, wherein the image sensor is further configured to be connected to glasses worn by a user, to enable the image sensor to move with a head of the user.

3. The apparatus of claim 1, wherein the image sensor is further configured to be movable with a head of the user and an aiming direction of the image sensor substantially coincides with a field of view of the user.

4. The apparatus of claim 1, wherein the image sensor is further configured to capture multiple images of text on an object in a field of view of the user.

5. The apparatus of claim 1, wherein the recognized representation includes audible reading of the text.

6. The apparatus of claim 1, wherein the optical character recognition is performed separately on the first image and the second image.

7. The apparatus of claim 1, wherein image data for the first image and the second image are combined and thereafter, optical character recognition is performed on the combined image data.

8. The apparatus of claim 1, wherein the at least one processor device is further configured to receive an additional plurality of images and to reconstruct text from the first image, the second image, and the additional plurality of images.

9. The apparatus of claim 1, wherein the at least one processor device is further configured to compare a plurality of sets of image regions proximate to each other, and based on statistics related to the plurality of sets of image regions recognize an associated character.

10. The apparatus of claim 1, wherein the at least one processor device is further configured to perform a layout analysis on the text to identify curved areas.

11. The apparatus of claim 1, wherein the at least one processor device is further configured to derive information from a shade pattern on the curved surface and to use the information when initiating the optical character recognition.

12. The apparatus of claim 1, wherein the at least one processor device is further configured to determine that the text is found on a curved surface and cause audible feedback to be outputted to the user, wherein the audible feedback prompts the user to enable capturing of images from a plurality of perspectives.

13. The apparatus of claim 1, wherein the at least one processor device is further configured to determine that the combined results of the optical character recognition do not include an end of a line, and upon receiving a third image of a third perspective of the text, provide the user with a recognized representation of the end of the line.

14. An apparatus for recognizing text on a surface of a curved object, the apparatus comprising:
    an image sensor configured to capture from an environment of a user a video stream; and
    at least one processor device configured to:
        identify the curved object contains a curved surface based on the video stream;
        determine that text is found on the identified curved surface;
        process a first frame of the video stream having a first perspective of text on the curved surface, wherein the first frame includes a first portion of text on the curved surface, the first portion of text including skewed characters that are unrecognizable using an optical character recognition process due to a curvature of the first portion of text on the curved surface viewed from the first perspective, and wherein the first frame includes a second portion of text recognizable using the optical character recognition process;

identify a second frame of the video stream having a second perspective of the text on the curved surface, wherein the second frame includes the first portion of text in a form capable of recognition in the optical character recognition process;

perform optical character recognition on the second portion of text in the first frame and the first portion of text in the second frame;

combine results of the optical character recognition on the second portion of text in the first frame and the first portion of text in the second frame;

combine results of the optical character recognition on the second portion of text in the first frame and on the first portion of text in the second frame; and provide the user with a recognized representation of the text on the curved surface, including a recognized representation of the second portion of text in the first image and the first portion of text in the second image.

15. The apparatus of claim 14, wherein the curved object includes a display of an electric device.

16. The apparatus of claim 14, wherein the curved object includes at least one of: a food product, a beverage, and pharmaceutical drugs, and the text is included on a label associated with the curved object.

17. The apparatus of claim 14, wherein the image sensor is further configured to be movable with a head of a user, and the video stream substantially coincides with a field of view of the user.

18. The apparatus of claim 14, wherein the at least one processor device is further configured to combine the results of the optical character recognition on the first frame and on the second frame.

19. The apparatus of claim 14, wherein the recognized representation includes audible reading of the text.

20. The apparatus of claim 14, wherein the second frame is subsequent but not consecutive to the first frame.

21. The apparatus of claim 14, further comprising a rechargeable mobile power source for powering at least the image sensor, wherein the rechargeable mobile power source is contained within a housing that holds the at least one processor device.

22. A method for recognizing text on a surface, the method comprising:

capturing a plurality of images at an initial resolution from an environment of a user;

identifying the surface is a curved surface based on at least one of the plurality of images;

determining that text is found on the identified curved surface;

receiving a first image of a first perspective of text on the curved surface, wherein the first image includes a first portion of text on the curved surface, the first portion of text including skewed characters that are unrecognizable in an optical character recognition process due to a curvature of the first portion of text on the curved surface viewed from the first perspective, and wherein the first image includes a second portion of text recognizable in the optical character recognition process;

receiving a second image of a second perspective of the text on the curved surface, wherein the second image includes the first portion of text in a form capable of recognition in an optical character recognition process;

performing optical character recognition on the second portion of text in the first image and the first portion of text in the second image;

combining the results of the optical character recognition on the second portion of text in the first image and on the first portion of text in the second image; and providing the user with a recognized representation of the text, including a recognized representation of the second portion of text in the first image and the firs portion of text in the second image.

23. The method of claim 22, wherein the first image of the first perspective is captured at the initial resolution and the second image of the second perspective is captured at a second resolution higher than the initial resolution.

24. A non-transitory computer readable medium comprising computer implementable instructions, which when executed by a computer, cause the computer to perform a method for recognizing text on a surface, the method comprising:

capturing a plurality of images at an initial resolution from an environment of a user;

identifying the surface is a curved surface based on at least one of the plurality of images;

determining that text is found on the identified curved surface;

receiving a first image of a first perspective of text on the curved surface, wherein the first image includes a first portion of text on the curved surface, the first portion of text including skewed characters that are unrecognizable in an optical character recognition process due to a curvature of the first portion of text on the curved surface viewed from the first perspective, and wherein the first image includes a second portion of text recognizable in the optical character recognition process;

receiving a second image of a second perspective of the text on the curved surface, wherein the second image includes the first portion of text in a form capable of recognition in an optical character recognition process;

performing optical character recognition on the second portion of text in the first image and the first portion of text in the second image;

combining the results of the optical character recognition on the second portion of text in the first image and on the first portion of text in the second image; and providing the user with a recognized portion of the text, including a recognized representation of the second portion of text in the first image and the first portion of text in the second image.

* * * * *

UNITED STATES PATENT AND TRADEMARK OFFICE
CERTIFICATE OF CORRECTION

Page 1 of 1

PATENT NO.      : 9,213,911 B2
APPLICATION NO. : 14/136545
DATED           : December 15, 2015
INVENTOR(S)     : Wexler et al.

It is certified that error appears in the above-identified patent and that said Letters Patent is hereby corrected as shown below:

In the claims,
Claim 22, Col. 26, Line 18, "firs" should read as --first--.

Signed and Sealed this
Nineteenth Day of April, 2016

Michelle K. Lee
*Director of the United States Patent and Trademark Office*